US007527929B2

(12) United States Patent
McKernan et al.

(10) Patent No.: US 7,527,929 B2
(45) Date of Patent: May 5, 2009

(54) METHODS OF ISOLATING NUCLEIC ACIDS USING MULTIFUNCTIONAL GROUP-COATED SOLID PHASE CARRIERS

(75) Inventors: Kevin J. McKernan, Marblehead, MA (US); Erik Gustafson, Norwood, MA (US); Adrianne D. Brand, Wenham, MA (US)

(73) Assignee: Agencourt Bioscience Corporation, Beverly, MA (US)

( * ) Notice: Subject to any disclaimer, the term of this patent is extended or adjusted under 35 U.S.C. 154(b) by 196 days.

(21) Appl. No.: 11/194,072

(22) Filed: Jul. 29, 2005

(65) Prior Publication Data

US 2006/0177836 A1 Aug. 10, 2006

Related U.S. Application Data

(60) Provisional application No. 60/592,917, filed on Jul. 30, 2004.

(51) Int. Cl.
*C12Q 1/68* (2006.01)
(52) U.S. Cl. .......................................................... 435/6
(58) Field of Classification Search ........................ None
See application file for complete search history.

(56) References Cited

U.S. PATENT DOCUMENTS

| 4,554,088 | A | 11/1985 | Whitehead et al. |
|---|---|---|---|
| 4,628,037 | A | 12/1986 | Chagnon et al. |
| 4,672,040 | A | 6/1987 | Josephson |
| 4,695,393 | A | 9/1987 | Whitehead et al. |
| 4,698,302 | A | 10/1987 | Whitehead et al. |
| 5,057,426 | A | 10/1991 | Henco et al. |
| 5,234,809 | A | 8/1993 | Boom et al. |
| 5,443,989 | A | 8/1995 | Alvarez et al. |
| 5,561,064 | A | 10/1996 | Marquet et al. |
| 5,614,386 | A | 3/1997 | Metzker et al. |
| 5,665,554 | A | 9/1997 | Reeve et al. |
| 5,681,946 | A | 10/1997 | Reeve |
| 5,705,628 | A | 1/1998 | Hawkins |
| 5,804,684 | A | 9/1998 | Su |
| 5,808,041 | A | 9/1998 | Padhye et al. |
| 5,898,071 | A | 4/1999 | Hawkins |
| 5,939,291 | A | 8/1999 | Loewy et al. |
| 5,972,613 | A | 10/1999 | Somack et al. |
| 6,270,970 | B1 | 8/2001 | Smith et al. |
| 6,534,262 | B1 | 3/2003 | McKernan et al. |
| 6,534,363 | B2 | 3/2003 | Kim |
| 6,718,742 | B1 | 4/2004 | Baker |
| 2001/0018513 | A1 | 8/2001 | Baker |
| 2002/0106686 | A1 | 8/2002 | McKernan |
| 2003/0008320 | A1 | 1/2003 | Baker |
| 2003/0130499 | A1 | 7/2003 | Baker |
| 2003/0235839 | A1 | 12/2003 | McKernan et al. |
| 2004/0197780 | A1 | 10/2004 | McKernan et al. |
| 2004/0214175 | A9 | 10/2004 | McKernan et al. |
| 2006/0003357 | A1 | 1/2006 | McKernan et al. |
| 2006/0024701 | A1 | 2/2006 | McKernan |
| 2006/0078923 | A1 | 4/2006 | McKernan et al. |
| 2006/0177836 | A1 | 8/2006 | McKernan et al. |
| 2007/0054285 | A1 | 3/2007 | McKernan et al. |

FOREIGN PATENT DOCUMENTS

| DE | 199 37 607 A1 | 2/2001 |
|---|---|---|
| EP | 0 818 461 | 1/1998 |
| WO | WO 91/12079 | 8/1991 |
| WO | WO 93/25709 | 12/1993 |
| WO | WO 95/04140 | 2/1995 |
| WO | WO 95/13368 A | 5/1995 |

(Continued)

OTHER PUBLICATIONS

Alderton, R. P., et al., "Magnetic Bead Purification of M13 DNA Sequencing Template," *Analytical Biochemistry*, 201:166-169 (1992).
Birnboim, H. C. and Doly, J., "A Rapid Alkaline Extraction Procedure for Screening Recombinant Plasmid DNA," *Nucleic Acids Research*, 7(6):1513-1523 (1979).
Birnboim, H.C., "A Rapid Alkaline Extraction Method for the Isolation of Plasmid DNA," *Methods in Enzymology*, 100:243-255 (1983).
Boom, R., et al., "Rapid and Simple Method for Purification of Nucleic Acids," *Journal of Clinical Microbiology*, 28(3):495-503 (1990).
Cole, "Purification of Plasmid and High Molecular Mass DNA Using PEG-Salt Two-Phase Extraction," *BioTechnqiues*, 11(1):18, 20, 22, 24 (1991).

(Continued)

*Primary Examiner*—James Martinell
(74) *Attorney, Agent, or Firm*—Jeffry K. Russell; Hamilton, Brook, Smith & Reynolds, P.C.

(57) ABSTRACT

The present invention is directed to a method of isolating a target species (e.g., target nucleic acid species) from a mixture. In the methods of the present invention, the mixture is combined with solid phase carriers having a surface comprising multiple functional groups one of which reversibly and selectively binds the target species. In a particular embodiment, the mixture is combined with solid phase carriers having a first functional group which reversibly binds nucleic acids and a second functional group which selectively and reversibly binds the target nucleic acid species, thereby producing a first combination. The first combination is maintained under conditions appropriate for binding of the nucleic acids to the first functional group and binding of the target nucleic acid species to the second functional group. The solid phase carriers are separated from the first combination, and combined with an agent (e.g., buffer) that selectively removes (e.g., elutes) either the nucleic acid from the first functional group or the target nucleic acid species from the second functional group of the solid phase carriers, thereby isolating a target nucleic acid species from a mixture comprising a plurality of nucleic acid species.

46 Claims, 22 Drawing Sheets
(19 of 22 Drawing Sheet(s) Filed in Color)

FOREIGN PATENT DOCUMENTS

| | | |
|---|---|---|
| WO | WO 95/21250 | 8/1995 |
| WO | WO 96/09379 | 3/1996 |
| WO | WO 96/18731 A | 6/1996 |
| WO | WO 98/05767 | 2/1998 |
| WO | WO 98/16653 | 4/1998 |
| WO | WO 98/31840 | 7/1998 |
| WO | WO 99/54340 A | 10/1999 |
| WO | WO 99/58664 A | 11/1999 |
| WO | WO 02/055727 A2 | 7/2002 |
| WO | WO 02/055727 A3 | 7/2002 |
| WO | WO 03/085091 A2 | 10/2003 |
| WO | WO 2004/090132 A2 | 10/2004 |
| WO | WO 2004/090132 A3 | 10/2004 |
| WO | WO 2006/015326 A2 | 2/2006 |
| WO | WO 2007/035750 | 3/2007 |

OTHER PUBLICATIONS

Deggerdal, A., and Larsen, F., "Rapid Isolation of PCR-Ready DNA from Blood, Bone Marrow and Cultured Cells, Based on Paramagnetic Beads," *BioTechniques*, 22:554-557 (Mar. 1997).

Dynal Catalog, pp. 78-79 and 138 (1995).

Fry, G., et al., "A New Approach to Template Purification for Sequencing Applications Using Paramagnetic Particles," *BioTechniques*, 13(1):124-131 (1992).

Hawkins, Trevor, "M13 Single-Stranded Purification Using A Biotinylated Probe and Streptavidin Coated Magnetic Beads," *J. DNA Sequencing and Mapping*, 3:65-69 (1992).

Hawkins, T.L., et al., "DNA purification and isolation using a solid-phase," *Nucleic Acids Research*, 22(21):4543-4544 (1994).

Hawkins, T.L., et al., "A Magnetic Attraction to High-Throughput Genomics," *Science*, 276:1887-1890 (Jun. 20, 1997).

Heller, et al., "Capillary Electrophoresis of Proteins and Nucleic Acids in Gels and Entangled Polymer Solutions," *Journal of Chromatography 698*:19-31 (1995).

Ish-Horowicz, D. and Burke, J. F., "Rapid and Efficient Cosmid Cloning," *Nucleic Acids Research*, 9(13):2989-2997 (1981).

Ito, T. et al., "Sequence-Specific DNA Purification by Triplex Affinity Capture," *Proceedings of the National Academy of Sciences of USA*, 89:495-498 (1992).

Levison, P.R., et al., "Recent developments of magnetic beads for use in nucleic acid purification," *Journal of Chromatography A*, 816:107-111 (1998).

Lis, J., et al., "Size Fractionation of Double Stranded DNA by Precipitation with Polyethylene Glycol," *Nucleic Acids Res.* 2(3):383-389 (1975).

Lis, J. T. "Fractionation of DNA Fragments by Polyethylene Glycol Induced Precipitation," *Methods in Enzymology*, 65:346-353 (1980).

Paithankar, K. R. and Prasad, K. S. N. "Precipitation of DNA by Polyethylene Glycol and Ethanol," *Nucleic Acids Research* 19(6):1346 (1991).

Prober, et al., "A system for Rapid DNA Sequencing with Fluorescent Chain—Terminating Dideoxynucleotides," *Science*, 238:336-341 (1987).

Pulleyblank, D., et al., "A method for the purification of *E. coli* plasmid DNA by homogeneous lysis and polyethylene glycol precipitation," *Molec. Biol. Rep.*, 9:191-195 (1983).

Sambrook, et al., "Molecular Cloning," *Cold Spring Harbor Laboratory Press*, p. 11.33 and E.10 (1989).

Takabatake, T., et al., "The Use of Purine-Rich Oligonucleotides in Triplex-Mediated DNA Isolation and Generation of Unidirectional Deletions," *Nucleic Acids Research* 20(21):5853-5854 (1992).

Wilson, R.K., "High-Throughput Purification of M13 Templates for DNA," Short Technical Report, *Bio Techniques* 15(3):414, 416, 418, 420, 422 (1993).

| Condition | EU / mL | DNA mg/mL | EU / mg DNA | % EU of control |
|---|---|---|---|---|
| Untreated | 628.2 | 0.2 | 2886.5 | 100.0 |
| Magnesil Silica | 550.9 | 0.5 | 1055.2 | 36.6 |
| CM beads | 633.0 | 0.3 | 1857.7 | 64.4 |
| PMXB-agarose | 621.5 | 0.3 | 1979.1 | 68.6 |
| PMXB + CM beads | 612.7 | 0.2 | 2659.4 | 92.1 |
| PMXB/CM beads | 0.5 | 0.1 | 3.6 | 0.1 |

| Treatment | EU / mL | DNA mg/mL | EU / mg DNA | % EU of control |
|---|---|---|---|---|
| Control | 2540.9 | 0.5 | 5286.1 | 100.0 |
| Magnesil silica beads | 1214.2 | 0.4 | 2844.3 | 53.8 |
| PMX-B/CM beads, 1hr | 96.7 | 0.2 | 505.8 | 9.6 |
| LALF Pp/CM beads, 1 hr | 58.8 | 0.3 | 178.8 | 3.4 |
| LALF Lp/CM beads, 1 hr | 65.0 | 0.3 | 257.9 | 4.9 |
| LALF Sc/CM beads, 1 hr | 50.0 | 0.3 | 183.4 | 3.5 |

| | PMX-B 0ug/mg | PMX-B 3.3ug/mg | PMX-B 6.8ug/mg | PMX-B 10ug/mg | PMX-B 11.2ug/mg | CM Beads | CosMcPrep |
|---|---|---|---|---|---|---|---|
| [DNA] in ng/ul = ug/ml | 386 | 405 | 344 | 338 | 406 | 626 | 536 |
| Total DNA in ug | 19.32 | 20.25 | 17.21 | 16.88 | 20.30 | 31.28 | 26.80 |
| EU LAL/ml eluate | 16580 | 1313 | 463 | 824 | 566 | 29092 | 31409 |
| EU LAL/ug DNA | 42.90 | 3.24 | 1.35 | 2.44 | 1.39 | 46.50 | 58.61 |
| EU LAL/mg DNA | 42903 | 3242 | 1346 | 2440 | 1395 | 46497 | 58608 |

METHODS OF ISOLATING NUCLEIC ACIDS USING MULTIFUNCTIONAL GROUP-COATED SOLID PHASE CARRIERS

RELATED APPLICATION

This application claims the benefit of U.S. Provisional Application No. 60/592,917, filed Jul. 30, 2004. The entire teachings of the above application are incorporated herein by reference.

BACKGROUND OF THE INVENTION

Many molecular biology applications, such as capillary electrophoresis, nucleotide sequencing, reverse transcription cloning and gene therapy protocols, which contemplate the transfection, transduction or microinjection of mammalian cells, require the isolation of high quality nucleic acid and peptide preparations. A need exists for methods which produce such high quality nucleic acid and peptide preparations.

SUMMARY OF THE INVENTION

The present invention is directed to a method of selectively isolating a target species of nucleic acid molecule present in a mixture, comprising combining the mixture with solid phase carriers having a surface comprising a first functional group which binds nucleic acids and a second functional group which selectively binds the target species of nucleic acid, thereby producing a first combination. The first combination is maintained under conditions appropriate for binding of the nucleic acids to the first functional group. The solid phase carriers are removed from the first combination, and combined with an agent that removes (elutes) the nucleic acid from the first functional group of the solid phase carriers and promotes (allows, causes) binding of the target species of nucleic acid to the second functional group of the solid phase carriers, thereby producing a second combination. The solid phase carriers are separated from the second combination, thereby isolating the target species of nucleic acid present in the mixture comprising nucleic acids.

The present invention is also directed to a method of selectively isolating a target species of nucleic acid molecule present in a mixture comprising nucleic acids, comprising combining the mixture with solid phase carriers having a surface comprising a first functional group which binds nucleic acids and a second functional group which selectively binds the target species of nucleic acid, thereby producing a first combination. The first combination is maintained under conditions appropriate for binding of the nucleic acids to the first functional group. The solid phase carriers are removed from the first combination, and combined with a first agent that removes the nucleic acid from the first functional group of the solid phase carriers, and a second agent that allows binding of the target species of nucleic acid to the second functional group of the solid phase carriers, thereby producing a second combination. The solid phase carriers are separated from the second combination, thereby isolating the target species of nucleic acid present in the mixture comprising nucleic acids.

In one embodiment, the invention is directed to a method of isolating mRNA present in a mixture comprising nucleic acids, comprising combining the mixture with solid phase carriers having a surface comprising a first functional group which binds nucleic acids and a second functional group which selectively binds mRNA, thereby producing a first combination. The first combination is maintained under conditions appropriate for binding of the nucleic acids to the first functional group. The solid phase carriers are separated from the first combination and combined with an agent that removes the nucleic acid from the first functional group of the solid phase carriers and binds the mRNA to the second functional group of the solid phase carriers, thereby producing a second combination. The solid phase carriers are removed from the second combination, thereby isolating mRNA present in a mixture comprising nucleic acids.

The present invention is also directed to a method of isolating mRNA present in a mixture comprising nucleic acids, comprising combining the mixture with solid phase carriers having a surface comprising a first functional group which binds nucleic acids and a second functional group which selectively binds mRNA, thereby producing a first combination. The first combination is maintained under conditions appropriate for binding of the nucleic acids to the first functional group. The solid phase carriers are removed from the first combination and combined with a first agent that removes the nucleic acid from the first functional group of the solid phase carriers, and a second agent that allows binding of the mRNA to the second functional group of the solid phase carriers, thereby producing a second combination. The first and second agent can be added simultaneously or sequentially. The solid phase carriers are separated from the second combination, thereby isolating mRNA present in a mixture comprising nucleic acids.

A method of separating globin RNA from nucleic acid present in a mixture is also encompassed by the present invention. The method comprises combining the mixture with solid phase carriers having a surface comprising a first functional group which binds nucleic acids and a second functional group which selectively binds globin RNA, thereby producing a first combination. The first combination is maintained under conditions appropriate for binding of the nucleic acids to the first functional group. The solid phase carriers are separated from the first combination and combined with at least one agent that removes the nucleic acid from the first functional group of the solid phase carriers and binds the globin RNA to the second functional group of the solid phase carriers, thereby producing a second combination. The solid phase carriers are separated from the second combination, thereby isolating globin RNA present in a mixture comprising nucleic acids. In a particular embodiment, the solid phase carriers are combined with a first agent that removes the nucleic acid from the first functional group of the solid phase carriers, and a second agent that allows binding of the globin RNA to the second functional group of the solid phase carriers, thereby producing the second combination. The first and second agent can be added simultaneously or sequentially. In another embodiment, the first functional group is COOH and the second functional group is an oligonucletoide comprising a sequence that is complementary to globin RNA sequence.

In a particular embodiment, the invention is directed to a method of separating globin RNA from nucleic acid present in a mixture, comprising combining the mixture with biotin labeled oligonucleotides comprising sequences that are complementary to globin RNA sequences present in the mixture, thereby producing a first combination. The first combination is maintained under conditions in which hybridization occurs between the oligonucleotides and the globin RNA, and combined with solid phase carriers having a first functional group that binds nucleic acid and a second functional group that selectively binds biotin, thereby producing a second combination. The second combination is maintained under conditions in which the nucleic acid binds to the first functional groups and the oligonucletoides which are hybridized to the globin RNA, bind to the second functional group of the solid phase carriers. The solid phase carriers are separated from the second combination and combined with an agent that elutes the nucleic acid from the first functional group, thereby separating globin RNA from nucleic acid present in the mixture.

The present invention is also directed to a method of separating endotoxin from nucleic acid in a mixture, comprising combining the mixture with solid phase carriers having a surface comprising a first functional group which binds nucleic acids and a second functional group which selectively binds endotoxin, thereby producing a first combination. The first combination is maintained under conditions appropriate for binding of the nucleic acids to the first functional group and binding of endotoxin to the second functional group. The solid phase carriers are separated from the first combination and combined with at least one agent that removes the nucleic acid from the first functional group of the solid phase carriers, thereby producing a second combination. The solid phase carriers, to which the endotoxin is still bound, are separated from the second combination, thereby separating endotoxin from nucleic acid present in the mixture. In a particular embodiment, the first functional group is COOH and the second functional group is selected from the group consisting of: polymyxin B, native *Limulus* anti-LPS factor (LALF) and recombinant LALF.

In a particular embodiment, the invention is directed to a method of separating endotoxin from nucleic acid in a mixture comprising combining the mixture with solid phase carriers having a surface comprising a first functional group which binds nucleic acids and a second functional group which selectively binds endotoxin, thereby producing a first combination. The first combination is maintained under conditions appropriate for binding of endotoxin to the second functional group. The solid phase carriers are separated from the first combination. Solid phase carriers having a surface comprising a functional group which binds nucleic acids are combined with the first combination, thereby producing a second combination. The second combination is maintained under conditions appropriate for binding of nucleic acid to the functional group of the solid phase carriers and the solid phase carriers are separated from the second combination, thereby separating endotoxin from nucleic acid present in the mixture.

The present invention is also directed to a method of isolating nucleic acid of an organism comprising combining the organism with solid phase carriers having a surface comprising a first functional group which binds the organism and a second functional group that binds nucleic acid, thereby producing a first combination. The first combination is maintained under conditions in which the organism binds to the first functional group. The solid phase carriers are separated from the first combination and combined with an agent that lyses the organism and binds the nucleic acid of the organism to the second functional group, thereby producing a second combination. The second combination is maintained under conditions in which the organism is lysed and the nucleic acid of the organism binds to the second functional group, thereby isolating the nucleic acid of the organism.

The present invention also relates to a method of separating forward extension products and reverse extension products of a sequencing reaction comprising combining a sequencing reaction mixture which comprises forward extension products and reverse extension products with solid phase carriers having a surface comprising a first functional group which selectively binds the forward extension products and a second functional group which binds nucleic acid, thereby producing a first combination. The first combination is maintained under conditions appropriate for binding of the forward extension products to the first functional group and binding of the reverse extension products to the second functional group. The solid phase carriers are separated from the first combination and combined with a buffer that selectively elutes the reverse extension products from the second functional group of the solid phase carriers, thereby producing a second combination. The solid phase carriers are separated from the second combination, thereby separating forward extension products and reverse extension products of the sequencing reaction.

The present invention also relates to a method of separating forward extension products and reverse extension products of a sequencing reaction comprising combining a sequencing reaction mixture which comprises forward extension products and reverse extension products with solid phase carriers having a surface comprising a first functional group which binds nucleic acid and a second functional group that selectively binds the forward extension products, thereby producing a first combination. The first combination is maintained under conditions appropriate for binding of the forward extension products to the second functional group and binding of the reverse extension products to the first functional group. The solid phase carriers are separated from the first combination and combined with a buffer that selectively elutes the revese extension products from the first functional group of the solid phase carriers, thereby producing a second combination. The solid phase carriers are separated from the second combination, thereby separating forward extension products and reverse extension products of the sequencing reaction.

In a particular embodiment, the present invention relates to a method of separating forward extension products and reverse extension products of a sequencing reaction comprising combining a sequencing reaction mixture which comprises forward extension products and reverse extension products with solid phase carriers having a surface comprising a first functional group which selectively binds the forward extension products and a second functional group which binds nucleic acid, thereby producing a first combination. The first combination is maintained under conditions appropriate for binding of the forward extension products to the first functional group. The solid phase carriers are separated from the first combination, thereby producing a second mixture comprising the reverse extension products. The solid phase carriers are combined with a buffer that selectively elutes the forward extension products from the first functional group of the solid phase carriers, thereby producing a second combination. The solid phase carriers are separated from the second combination and combined with the second mixture, thereby producing a third combination. The third combination is maintained under conditions appropriate for binding of the reverse extension products to the second functional group and combined with a buffer that selectively elutes the reverse extension products from the second functional group of the solid phase carriers, thereby separating forward extension products and reverse extension products of the sequencing reaction.

The present invention is also directed to kits for use in the methods of the present invention. In one embodiment, the kit comprises bifunctional beads and a cell lysis buffer. In a particular embodiment, the kit comprises bifunctional magnetic microparticles comprising COOH groups and oligo dT groups and cell lysis buffer. In another embodiment, the kit comprises bifunctionl magnetic microparticles comprising COOH groups and streptavidin groups, and buffers such as binding and/or wash buffers. In another embodiment, the kit comprises heterobifunctional magnetic microparticles comprising COOH functional groups and polymyxin B functional groups. In yet another embodiment, the kit comprises heterobifunctional magnetic microparticles comprising COOH functional groups and LALF functional groups. The kits of the present invention can further comprise additional buffers such as wash buffers and elution buffers.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1:
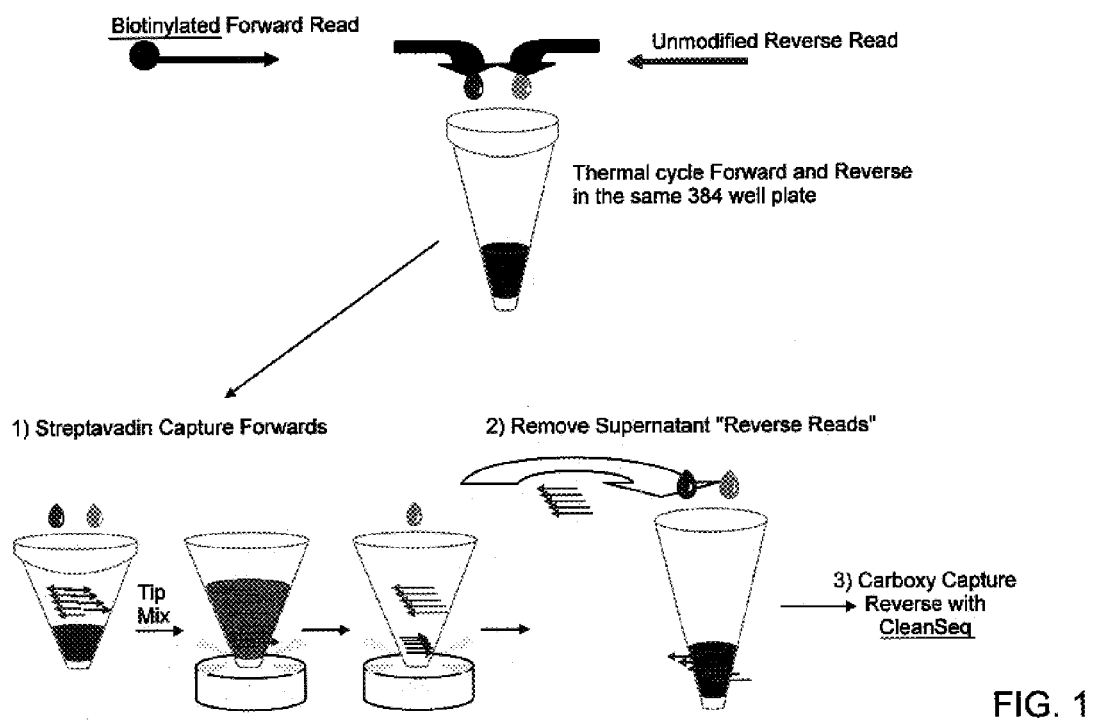
FIG. 1 is a schematic of a solid phase based purification procedure using two functional groups on magnetic beads which separates a duplex sequencing reaction into its respective forward and reverse primers.

The present invention is based, in part, on the discovery that at least two molecules present in a mixture can be separated using a solid phase carrier having a surface comprising at least two, distinct (heterologous) functional groups (multifunctional groups). Two separate binding events occur wherein each molecule binds to a distinct functional group present on the solid phase carrier, thereby providing for the separation of the molecules. The binding events that occur on the solid phase carrier can occur simultaneously (in one step) or sequentially (in more than one step).

Accordingly, the present invention is directed to methods of separating or isolating a (one or more) target species present in a mixture of species using solid phase carriers having a surface comprising at least two, distinct (heterologous) functional groups (multifunctional groups), wherein the target species binds to one of the functional groups and the species from which the target species is being separated binds to another functional group that is distinct from the group to which the target species is bound. Examples of target species present in a mixture that can be isolated using the methods of the present invention include nucleic acids (e.g., DNA, RNA), peptides (e.g., polypeptide, protein), saccharides (e.g., polysachharides, lipopolysaccharides), whole organisms (e.g., virus) and contaminants. Examples of suitable mixtures or starting material which comprise the target species (e.g., a target nucleic acid species) for use in the methods of the present invention include biological samples (e.g., blood, tissue, tissue lysates, cells, cell lysates), and the products of nucleic acid manipulations (e.g., sequencing reactions) used for molecular diagnostics, expression profiling, genotyping and transfection.

The methods are particularly suited for separating or isolating a target nucleic acid species in a mixture from other species or components present in the mixture, using solid phase carriers having a surface comprising at least two, distinct functional groups, wherein the target nucleic acid species binds to one of the functional groups and the one or more component(s) from which the target species is being separated binds to another functional group that is distinct from the functional group to which the target nucleic acid species is bound. The other components in the mixture from which the target nucleic acid species can be separated include such components as other nucleic acid species, peptides, saccharides, whole organisms and contaminants.

The multifunctional solid phase carriers of the present invention can be used to separate or isolate nucleic acid species and peptide species present in a mixture comprising a plurality of nucleic acid species and peptide species. In one embodiment, the present invention is directed to a method of isolating a target nucleic acid species from a mixture comprising a plurality of nucleic acid species and peptide species. In another embodiment, the present invention is directed to a method of isolating a target nucleic acid species from a mixture comprising a plurality of nucleic acid species. The mixture is combined with solid phase carriers having a surface comprising multiple functional groups which reversibly bind nucleic acid and peptides.

In a particular embodiment, the present invention is directed to a method of separating a (one or more) nucleic acid species in a mixture from a (one or more) peptide species in the mixture. The mixture is combined with solid phase carriers having a first functional group which reversibly binds nucleic acids and a second functional group which reversibly binds the peptide species, thereby producing a first combination. The first combination is maintained under conditions appropriate for binding of the nucleic acids to the first functional group and binding of the peptide species to the second functional group. The solid phase carriers are separated from the first combination, and combined with an agent (e.g., buffer) that selectively removes (e.g., elutes) either the nucleic acid from the first functional group or the peptide species from the second functional group of the solid phase carriers, thereby separating a nucleic acid species in a mixture from one or more peptide species in the mixture.

In another embodiment, the present invention is directed to a method of isolating a target nucleic acid species from a mixture comprising a plurality of nucleic acid species. The mixture is combined with solid phase carriers having a first functional group which reversibly binds nucleic acids and a second functional group which selectively and reversibly binds the target nucleic acid species, thereby producing a first combination. The first combination is maintained under conditions appropriate for binding of the nucleic acids to the first functional group and binding of the target nucleic acid species to the second functional group. In a particular embodiment, the second functional group has a higher affinity for the target nucleic acid species than the first functional group, and thus, the target nucleic acid species preferably binds to the second functional group. The solid phase carriers are separated from the first combination, and combined with an agent (e.g., buffer) that selectively removes (e.g., elutes) either the nucleic acid from the first functional group or the target nucleic acid species from the second functional group of the solid phase carriers, thereby isolating a target nucleic acid species from a mixture comprising a plurality of nucleic acid species.

The solid phase carriers can be separated from the first combination, and combined with an agent (e.g., buffer) that selectively removes (e.g., elutes) the target nucleic acid species from the second functional group of the solid phase carriers, thereby isolating a target nucleic acid species from a mixture comprising a plurality of nucleic acid species. That is, combining the solid phase carriers with the agent results in removal of the target nucleic acid species from the second functional group but not removal of nucleic acid bound to the first functional group. In the presence of the agent, the nucleic acid remains bound to the first functional group on the solid phase carriers.

Alternatively, the solid phase carriers can be separated from the first combination, and combined with an agent that selectively removes the nucleic acid species from the first functional group of the solid phase carriers, while the target nucleic acid remains bound to the second functional group on the solid phase carriers. That is, combining the solid phase carriers with the agent results in removal of the nucleic acid from the first functional group but not removal of the target nucleic acid species bound to the second functional group. The agent (e.g., a buffer; an enzyme) can result in, for example, either elution or degradation of the nucleic acid bound to the first functional group. The solid phase carriers to which are bound the target nucleic acid species are then removed, thereby isolating the target nucleic acid species from a mixture comprising a plurality of nucleic acid species. The target nucleic acid species can be eluted from the second functional group on the solid phase carriers.

In a particular embodiment, the present invention is directed to a method of isolating a target nucleic acid species present in a mixture comprising nucleic acids. The mixture is combined with solid phase carriers having a surface comprising a first functional group which reversibly binds nucleic acids and a second functional group which selectively and reversibly binds the target species of nucleic acid, thereby producing a first combination. The first combination is maintained under conditions appropriate for binding of the nucleic acids to the first functional group. In this embodiment, the nucleic acid in the sample, including the target nucleic acid species, bind to the first functional group. The solid phase carriers are separated from the first combination and can be combined with an agent that removes the nucleic acid from the first functional group of the solid phase carriers and promotes (allows) binding (selective binding) of the target nucleic acid species to the second functional group on the solid phase carriers, thereby producing a second combination. In the second combination, the target species nucleic acid is bound to the second functional group, while other nucleic acid remain in solution. Alternatively, the solid phase carriers which have been separated from the first combination can be combined with an agent that removes the nucleic acid from the first functional group, and a second agent that promotes (causes) the selective binding of the target species of nucleic acid to the second functional group of the solid phase carriers is added, thereby producing a second combination. The solid phase carriers are separated from the second combination, thereby isolating the target species of nucleic acid present in the mixture comprising nucleic acids.

The multifunctional solid phase carriers described herein can also be used to purify RNA from a mixture such as a cell or cell lysate. For example, mRNA and/or globin RNA can be isolated or separated from a mixture using the methods described herein.

In one embodiment, total nucleic acid present in the cell or cell lysate is bound to solid phase carriers which comprise free COOH groups and COOH groups to which oligo dT groups have been covalently attached as a second functional group, thereby isolating the nucleic acid in the mixture. Following nucleic acid isolation, the solid phase carriers are combined with a buffer (e.g., a low ionic strength buffer) which promotes elution of total nucleic acid and subsequent binding of the poly-A of the mRNA to the oligo-dT functional group on the solid phase carriers. The solid phase carriers can be removed and the mRNA can be eluted from the solid phase carriers, thereby isolating the mRNA. Prior to elution of the mRNA, the solid phase carriers can be washed with a suitable wash buffer.

In one embodiment, the invention is directed to a method of isolating mRNA present in a mixture comprising nucleic acids. The mixture is combined with solid phase carriers having a surface comprising a first functional group which binds nucleic acids and a second functional group which selectively binds mRNA, thereby producing a first combination. The first combination is maintained under conditions appropriate for binding of the nucleic acids to the first functional group. The solid phase carriers are separated from the first combination and combined with at least one agent that removes the nucleic acid from the first functional group of the solid phase carriers and allows binding of the mRNA to the second functional group of the solid phase carriers, thereby producing a second combination. The solid phase carriers are removed from the second combination, thereby isolating mRNA present in a mixture comprising nucleic acids. The mRNA can then be eluted from the solid phase carriers in a suitable elution buffer. In a particular embodiment, the solid phase carriers are combined with a first agent that removes the nucleic acid from the first functional group of the solid phase carriers, and a second agent that allows binding of the mRNA to the second functional group of the solid phase carriers, thereby producing the second combination.

The multifunctional solid phase carriers described herein can also be used to separate globin RNA from nucleic acid present in a mixture. Examples of globin RNA that can be isolated using the methods described herein include alpha, beta, delta, gamma, epsilon, theta and zeta globin RNA.

In one embodiment, the present invention relates to a method of removing globin nucleic acid sequences present in a mixture of nucleic acid, comprising combining he mixture with solid phase carriers having a first functional group which binds nucleic acids and a second functional group which selectively binds nucleic acids containing globin specific sequences, thereby producing a first combination. The first combination is maintained under conditions appropriate for binding of the nucleic acids to the first functional group. The solid phase carriers are separated from the first combination and combined with at least one agent that removes the nucleic acid from the first functional group of the solid phase carriers and promotes (allows) binding of globin containing sequences to the second functional group of the solid phase carriers, thereby producing a second combination. The solid phase carriers are removed from the second combination, thereby removing globin specific sequence from the second combination.

In another embodiment, the method of removing globin nucleic acid sequences present in a mixture of nucleic acid comprises combining the mixture with solid phase carriers having a first functional group which binds nucleic acids and a second functional group which selectively binds nucleic acids containing globin specific sequences, thereby producing a first combination. The first combination is maintained under conditions appropriate for binding of the nucleic acids to the first functional group. The solid phase carriers are separated from the first combination and combined with a first agent that removes the nucleic acid from the first functional group of the solid phase carriers. A second agent that allows selective binding of globin containing sequences to the second functional group of the solid phase carriers is added, thereby producing a second combination. The solid phase carriers are removed from the second combination, thereby removing globin specific nucleic acid sequence(s) from the second combination.

In another embodiment, the method of removing globin nucleic acid sequences present in a mixture of nucleic acid sequences comprises combining a mixture of nucleic acid sequences with biotin labeled oligonucleotides complementary in sequence to globin sequences under conditions that promote hybridization between the biotin labeled oligonucleotides and the globin sequences thereby producing a first combination. The first combination is combined with solid phase carriers having a first functional group that binds nucleic acid and a second functional group which selectively binds biotin, producing a second combination. This second combination is maintained under conditions appropriate for binding of the hybrids formed between the biotin labeled oligonucleotides and the globin sequences. An agent which promotes binding of the remaining nucleic acid to the first functional group is added, thereby producing a third combination. The solid phase carriers are removed from the third combination, washed, and combined with an agent that elutes nucleic acid bound to the first functional group, thereby separating globin sequences from the nucleic acid mixture.

The multifunctional solid phase carriers described herein can also be used to separate contaminants from nucleic acid in a mixture or sample. Introduction of high-throughput DNA preparation methods has fueled the growth of large-scale sequencing efforts and has resulted in the generation of a vast collection of genomic and expressed gene sequences. Further characterization of these sequences in vitro may be applied using high-throughput analysis of expressed genes for the evaluation of mammalian cell function (Ziauddin, J., et al., *Nature*, 411:107-110 (2001). Moreover, gene therapy studies in vivo using plasmid and BAC DNA have been widely applied in animal models for both the characterization of disease states and for the evaluation of potential therapeutic intervention (Nabel, G. J., et al., *Proc. Natl. Acad. Sci., USA,* 90:11307-11311 (1993)). Additionally, the increased understanding of genetic immunization using naked DNA vaccines has also held great promise as a novel therapeutic deliverable (Lewis, P. J., et al., *Adv. Virus Res.*, 54:129-188 (1999); Liu, M., *J. Intern. Med.,* 253:402-410 (2003)). Unfortunately, such applications and therapies are very sensitive to contaminants typically present in nucleic acid preparations. Standard methods of plasmid DNA isolation from bacteria, including alkaline lysis, high pressure (French Press) boiling, and the use of lysozyme or detergents will induce the release of lipopolysaccharide (LPS), or endotoxin, from the outer membrane of the bacteria along with plasmid DNA. The LPS will then form micelles with physical characteristics (density, size, and charge distribution) similar to plasmid DNA, and as a consequence, be carried through the purification steps along with the plasmid DNA. Contaminating endotoxins from *E. coli* host typically used to prepare DNA molecules has been shown to induce apoptosis during culture of mammalian cell in vitro (Kuwabara, T., *Apoptosis,* 9:467-474 (2004)), as well as toxic shock, sepsis and a variety of related clinical complications in vivo (DiPiro, J. T., *Am. J. Hosp. Pharm.,* 47:S6-10 (1990)). The transfection efficiency of endotoxin-containing DNA in mammalian cells such as HeLa, Huh7, COS7, and LNH is reduced significantly compared to endotoxin-free DNA (Weber, M., et al., *BioTechniques,* 19:930-940 (1995)).

Endotoxins are constituents of the outer-membrane of Gram-negative bacteria that contribute to the organization and stability of the outer membrane. First termed by R. Pfeiffer (1858-1945), endotoxin characterizes a class of lipopolysaccahrides (LPS) that have since been well characterized both structurally and chemically (Rietschel, et al., 1994). The general structure of all endotoxins is a polar heteropolysaccharide chain, covalently linked to a non-polar moiety (lipid A). As dominant bacterial membrane structures, endotoxins participate in the interaction of the bacterial cell with its surroundings. Endotoxins do not act directly against cells or organs but through activation of the immune system (Anspach 2001). When gram-negative bacteria gains access to a mammalian host, the presence of endotoxin activates the host's immune system and has been shown to be involved in the pathogenesis of inflammation and septic shock in the host. Small quantities of endotoxin have been shown to alter phenotypes of various cell types (Gould et al. 1984), particularly mononuclear, endothelial, smooth muscle cells and polymorphonuclear granulocytes and monocytes (Galanos and Freudenberg 1993; Galanos et al. 1992). These cell types respond to endotoxin presence by producing bioactive lipids, reactive oxygen species and various peptide inflammatory mediators (Rietschel et al., 1994). It is this type of cellular response that causes endotoxins to produce striking pathophysiological reactions when introduced into animals including high fever, vasodilation, diarrhea and, in extreme cases, fatal shock (Morrison, D. C., *Ann. Rev. Med.,* 38:417-432 (1987)).

In addition to toxic effects on cells from in vivo introduction of gram negative bacteria, endotoxin has been shown to exert toxicity on mammalian cells in vitro. Transfection efficiency of endotoxin contaminated DNA is hindered due to toxic effects of endotoxin on mammalian cells such as HeLa, Huh7, COS7 and LNH (Weber, M., et al., *Biotechniques,* 19:930-939, 1995). This toxicity is seen when introducing DNA using either adenovirus, glycerol or cationic lipid based trasnfections and is atrributed to the lipid A component of endotoxin. Lipid A itself has no consequences, but the introduction of endotoxin into the vesicular system, cytoplasm, or nucleus of cells during transfection leads to an apoptotic pathway (Cotton and Saltik, 1997). As could be expected, endotoxins also exert toxicity during introduction of DNA in vivo in processes such as microinjection and gene therapy research (Weber et al., 1995; Vukajlovich, S. W. et al., 1987;

Schleef, M. 1999). The adverse reactions make it imperative to remove endotoxin from drugs, injectables and other biological and pharmaceutical products as well as from plasmid DNA preparations. Studies on humans using such products have resulted in strict guidelines by the FDA which require that nucleic acids used for any therapeutic application have less than 300 EU/mg or 300 IU/mg (U.S. Pat. No. 6,297,371).

A number of peptide, proteins and receptor motifs interact strongly with endotoxins, and thus, can be used, in the methods of the present invenion. Some of these include lipopolysaccharide binding protein (LBP), bactericidal/permeability-increasing protein (BPI) (Beamer, L. J., *Protein Sci.*, 7:906-914 (1998)), polymyxin and polymyxin analogs (Jacobs, D. M., et al., *J. Immunol.*, 118:21-27)1997)), amyloid P component (de Haas, C. J., et al., *Infect. Immun.*, 67:2790-2796 (1999)), cationin protein 18 (de Haas, C. J., et al., *Biochem. Biophys. Res. Comm.*, 252:492-496 (1998)), MD-2 and Toll-like receptor (TLR) (Shimazu, R., et al., *J. Exp. Med.*, 189:1777-1782 (1999)), TLR2 (Sabroe, I., et al., *J. Immunol.*, 168:4701-4710 (2002)), CD14 (Soler-Rodriguez, A. M., et al., *J. Immunol.*, 164:2674-2683 (2000)), Bac7 (About, S., et al., *Cancer epidemiology, biomarkers and prevention*, 11:1130-1133 (2002), Liu, M. A., *J, Intern. Med.*, 253:402-410 (2003)), a synthetic peptide derived from a protein found in bovine neutrophils (Ghiselli, R., et al., *Shock*, 19:577-581 (2003)), *limulus* factor-C and synthetic peptides derived from Sushi3 domain thereof (Li. C., et al., *Protein Eng.*, 116:629-635 (2003)) and antibodies raised against the lipid A component of endotoxin (Helmerhorst, E. M., et al., *Infect. Immun.*, 66:870873 (1998); Holy, R. A., et al., *Science*, 298:129-149 (2002)).

One molecule that has been extensively used as an endotoxin absorbent is polymyxin B (PMXB), a cyclic cationic polypeptide antibiotic. PMXB binds stoiciometrically to the lipid A moiety of endotoxin molecules, primarily through the hydrophobic interactions (Srimal, S., et al., *Biochem. J.*, 315: 679-686 (1996)). Specifically, PMXB and endotoxin associate primarily due to interactions of a hydrophobic patch at one side of the peptide and Lipid A component of endotoxin (Srimal, et al. 1996).

Another particular molecule that can be used in the methods of the present invention is *Limulus* anti-LPS factor (LALF) isolated from the American Horseshoe crab (*Limulus polyphemus*). This is the protein used in the LAL assay to determine endotoxin levels. In the methods of the present invnetion, LALF native protein and recombinant protein (e.g., LALF expressed in *Pichia pastoris*; LALF exressed in *Saccharomyces cerevisiae*) can be used.

A protein or molecule which binds endotoxin can be adsorbed onto carboxy containing solid phase carrier via charge and hydrophobicity interactions. PXMB carries a net positive charge at pH<10, and readily associates with carboxy solid phase carriers by simple incubation of the molecule in the presence of MES buffer and a solid phase carrier solution (1% solids) for 24 hours.

In a particular embodiment, covalent coupling is used. Covalent coupling of a molecule which binds endotoxin (e.g., PMXB molecule) to a carboxy group on a solid phase carrier allows for a heterobifunctional solid phase carrier which comprises two distinct functional groups (e.g., COOH and PMXB) on the solid phase carrier surface each designed to target a different biochemical molecule. For example, by covalently coupling PMXB to carboxylated solid phase carriers, it is possible to drive endotoxin to the PMXB functional group on the solid phase carrier under low salt conditions and subsequently drive nucleic acid to the COOH functional group on the same solid phase carrier under different conditions. Once the solid phase carriers are separated from the mixture, and the supernatant removed, the DNA can be eluted from the COOH functional groups on the solid phase carrier under conditions in which the endotoxin remains attached to the PMXB functional groups on the same solid phase carrier.

In one embodiment, the invention relates to a method of removing endotoxin contamination from a nucleic acid solution by simultaneously binding nucleic acid and endotoxin to bi-functional solid phase carriers comprising an endotoxin binding group, such as PMXB or LALF proteins, and a nucleic acid binding group such as carboxyl groups. The solid phase carriers are added to a solution containing endotoxin and nucleic acid, such as a bacterial cleared lysate, under conditions (e.g., buffer conditions) in which binding of the nucleic acid to the carboxyl functional group and binding of endotoxin to the endotoxin binding functional group occurs. The solid phase carriers are removed from the solution and contacted with a buffer (e.g., a buffer of low ionic strength) which causes selective elution of nucleic acids from the solid phase carriers. The solid phase carriers, to which are still bound the endotoxin, are removed leaving a solution of purified (substantially pure) nucleic acid.

In another embodiment, the invention relates to a method of removing endotoxin contamination from a nucleic acid solution by simultaneously binding nucleic acid and endotoxin to bi-functional solid phase carriers comprising an endotoxin binding functional group, such as PMXB or LALF proteins, and a nucleic acid binding functional group such as carboxyl groups. The bi-functional solid phase carriers are added to a solution containing endotoxin and nucleic acid, such as a bacterial cleared lysate, in buffer conditions creating a first mixture which causes binding of the endotoxin to the endotoxin binding functional groups. The buffer conditions in the first mixture are adjusted to provide conditions in which nucleic acid binds to the nucleic acid binding functional group and endotoxin remains bound to the endotoxin binding functional group. The solid phase carriers are removed from the solution and mixed with a buffer (e.g., of low ionic strength) which causes selective elution of nucleic acids from the solid phase carriers. The solid phase carriers, to which the endotoxin remains bound, are removed leaving a solution of purified nucleic acid.

In yet another embodiment, the invention relates to a method of removing endotoxin contamination from a nucleic acid solution by adding bifunctional solid phase carriers containing an endotoxin binding functional group, such as PMXB or LALF proteins, and a nucleic acid binding functional group such as carboxyl groups, to a solution of nucleic acids and endotoxin such as a bacterial lysate, creating a first mixture in which endotoxin is bound to the solid phase carriers through the endotoxin binding functional group. The solid phase carriers are removed from solution leaving a second mixture of nucleic acids essentially purified from endotoxin. Bifunctional solid phase carriers are added to the second mixture under conditions which cause binding of the nucleic acid to the carboxy functional group creating a third mixture. Alternatively, solid phase carriers comprising a carboxy group can be added to create the thrid mixture. The solid phase carriers are removed from the third mixture and mixed with a buffer of low ionic strength to elute purified nucleic acid from the solid phase carriers.

The methods described herein can also be used to concentrate a virus from a solution and subsequently isolate viral nucleic acid. A polycationic polymer, such as the polymer polyethyleneimine (PEI) or poly-L-lysine (PLL), is covalently coupled to solid phase carriers containing a carboxyl functional group. Carboxyl groups are first activated by carbodiimide 1-ethyl-3-(3-dimethylaminopropyl)-carbodiimide (EDAC) and then reacted with free amino groups on the polymer. This produces a solid phase carrier with two functional groups, a polycation polymer for virus binding, and carboxyl groups for nucleic acid binding. The polymer modified bi-functional solid phase carriers are added to a volume of virus containing serum or lysate and mixed well creating a first mixture in which viral particles in the serum are concentrated on the surface of the solid phase carriers via interaction with the polymer. The solid phase carriers are separated and the serum supernatant is removed. To the solid phase carriers are added a lysis buffer containing, for example, 20 mM Tris pH 7.0, 1% Triton-X-100, 2% SLS, 10 mM DTT, isopropanol and an RNase inhibitor. This results in a second mixture in which virus is lysed, and upon lysis, viral nucleic acid becomes bound to the solid phase carriers via interaction with the carboxyl groups. The solid phase carriers are separated, and can be washed in a wash buffer and/or 70% ethanol. The solid phase carriers can be dried and the purified viral nucleic acid is eluted in a low ionic strength buffer.

In one embodiment, the present invention is directed to a method of isolating the nucleic acid of an organism (e.g, a pathogen, such as a virus, bacteria, fungus, parasite) comprising combining the organism with solid phase carriers having a surface comprising a first functional group which binds nucleic acids and a second functional group which selectively binds the organism, thereby producing a first combination. The first combination is maintained under conditions appropriate for binding of the organism to the second functional group; and the solid phase carriers are separated from the first combination. The solid phase carriers are combined with an agent that lyses the organism, and upon lysis, the nucleic acid of the organism is released and becomes bound to the first functional group on the solid phase carriers. The solid phase carriers are separated and the organism's nucleic acid can then be eluted from the solid phase carriers, thereby isolating the nucleic acid of the oraganism.

As used herein the term "isolating" is intended to mean that the material in question exists in a physical milieu distinct from that in which it occurs in nature and/or has been completely or partially separated, isolated or purified from other nucleic acid molecules.

As used herein the terms "nucleic acid" and "nucleic acid molecule" are used synonymously with the term polynucleotides and they are meant to encompass DNA (e.g., single-stranded, double-stranded, covalently closed, relaxed circular forms, genomic DNA, cDNA, plasmid DNA), RNA (e.g., single-stranded and double-stranded, mRNA), cRNA, antisense RNA, micro RNA, RNA/DNA hybrids and polyamide nucleic acids (PNAs).

A "solid phase carrier" is an entity that has, or to which can be added, a functional group (one or more) that reversibly binds the target species. The solid phase carrier is essentially insoluble under conditions in which a target species can be precipitated onto (can bind to) the solid phase carrier. Suitable solid phase carriers for use in the methods of the present invention have sufficient surface area to permit efficient binding of the target species to the functional group(s) on the carriers, and are further characterized by having surfaces which are capable of reversibly binding the target species. Suitable solid phase carriers include, but are not limited to, microparticles (e.g., beads), fibers and supports which have an affinity for a target species, such as nucleic acid, and which can embody a variety of shapes, that are either regular or irregular in form, and preferably have a shape that maximizes the surface area of the solid phase, and embodies a carrier which is amenable to microscale manipulations. In one embodiment, the solid phase carrier is a magnetic microparticle (e.g., a paramagnetic (magnetically responsive) microparticle).

As used herein, "paramagnetic microparticles" refer to microparticles which respond to an external magnetic field (e.g., a plastic tube or a microtiter plate holder with an embedded rare earth (e.g., neodymium) magnet) but which demagnetize when the field is removed. Thus, the paramagnetic microparticles are efficiently separated from a solution using a magnet, but can be easily resuspended without magnetically induced aggregation occurring. Particular paramagnetic microparticles comprise a magnetite rich core encapsulated by a pure polymer shell. In one embodiment, suitable paramagnetic microparticles comprise about 20-35% magnetite/encapsulation ratio. For example, magnetic particles comprising a magnetite/encapsidation ration of about 23%, 25%, 28% 30% 32% or 34% are suitable for use in the present invention. Magnetic particles comprising less than about a 20% ratio are only weakly attracted to the magnets used to accomplish magnetic separations. Depending on the nature of the mixture used in the methods of the present invention, paramagnetic microparticles comprising a higher percentage of magnite should be considered. The use of encapsulated paramagnetic microparticles, having no exposed iron, or $Fe_3O_4$, on their surfaces, eliminates the possibility of iron interfering with polymerase function in certain downstream manipulations of the isolated nucleic acid. However the larger the magnetite core the higher the chance of encapsulation leakage (e.g., release of iron oxides).

Suitable paramagnetic microparticles should be of a size that their separation from solution, for example by magnetic means or by filtration, is not difficult. In addition, preferred paramagnetic microparticles are those that are not so large that their surface area is minimized or that they are unsuitable for microscale manipulation. Suitable sizes range from about 0.1µ mean diameter to about 100 µ mean diameter. A preferred size is about 1.0µ mean diameter. Suitable magnetic microparticles for use in the instant invention can be obtain, for example, from Agencourt Biosciences, Polysciences, Bioclone, Seradyne, Bangs Laboratories Inc., Fishers, and IN (e.g., estapor® carboxylate-modified encapsulated magnetic microspheres).

In one embodiment, the target species in the mixture binds non-specifically to at least one functional group on the solid phase carrier. "Non-specific binding" refers to binding of different target species molecules (e.g., different species of nucleic acid, such as nucleic acid which differ in size) with approximately similar affinity to the functional groups on the solid phase carriers, despite differences in the structure (e.g., nucleic acid sequence) or size of the different target species molecules. The binding can occur, for example, via facilitated adsorption. As used herein, "facilitated adsorption" refers to a process whereby a precipitating reagent (e.g., a poly-atylene glycol, ethanol, isopropanol) is used to promote the precipitation and subsequent adsorption of a species of DNA molecules, which were initially in mixture, onto the surface of a solid phase carrier.

In another embodiment, the target species in the mixture binds specifically (selectively) to at least one functional group on the solid phase carrier. "Specific binding" or "selective binding" refers to binding of, for example, particular nucleic acid molecules (e.g., a target nucleic acid species) to one or more functional groups on the solid phase carriers to the exclusion of other nucleic acid species in a mixture. In this embodiment, the functional group has a greater affinity for particular nucleic acid molecules (e.g., the target nucleic acid species) than other functional groups on the solid phase carrier. Such reversible interactions include an interaction between two binding partners. For example, the interaction can be between two binding partners which are conventionally utilized for the purpose of isolating particular biomolecules based on their composition or sequence (e.g., streptavidin/biotin, antibody/antigen, ligand receptor or a sequence-specific interaction such as hybridization of complementary sequences).

The solid phase carriers used in the methods of the present invention have a functional group coated surface. In particular, the surface of the solid phase carriers for use in the methods of the present invention comprise multiple (at least two), distinct functional groups. As used herein, the term "functional group-coated surface" refers to a surface of a solid phase carrier that is coated with functional groups or moieties which reversibly bind a target molecule present in a mixture, such as nucleic acid (e.g., DNA, RNA or polyamide nucleic acids (PNA)), peptides, saccharides, whole organisms, and contaminants, either directly (the functional group binds the nucleic acid or peptides) or indirectly (the functional group (e.g., streptavidin) binds a group that is linked to the nucleic acid (e.g., biotin) or peptides).

Methods for coating solid phase carriers with functional groups, either directly or indirectly, are known in the art. For example, the functional groups (e.g., COOH) can coat a solid phase carrier during formation of the solid phase carrier. See, for example, U.S. Pat. No. 5,648,124 which is incorporated herein by reference. In additional, solid phase carriers can be coated with functional groups by covalently coupling a functional group (one or more) to a COOH group (one or more) on the solid phase carrier. A particular example of a functional group coated surface is a surface which is coated with moieties which each have a free functional group which is bound to the amino group of the amino silane of the microparticle; as a result, the surfaces of the microparticles are coated with the functional group containing moieties. The functional group acts as a bioaffinity adsorbent for precipitated nucleic acid (e.g., polyalkylene glycol precipitated DNA) or peptides.

In one embodiment, at least one of the functional groups is a carboxylic acid (COOH). A suitable moiety with a free carboxylic acid functional group is a succinic acid moiety in which one of the carboxylic acid groups is bonded to the amine of amino silanes through an amide bond and the second carboxylic acid is unbonded, resulting in a free carboxylic acid group attached or tethered to the surface of the solid phase carrier. Carboxylic acid-coated magnetic particles are commercially available from, for example, Polysciences, Inc. Carboxy groups play a key role in effective elution of nucleic acid from a solid phase carrier. Carboxy groups have a pKa of 4.7 so they are negatively charged at neutral pH. Nucleic acid, such as DNA, is negatively charged, and in the absence of any crowding reagents or salt, nucleic acid repels itself from the microparticles at neutral pH.

Suitable solid phase carriers having a functional group coated surface that reversibly binds nucleic acid molecules are for example, magnetically responsive solid phase carriers having a functional group-coated surface, such as, but not limited to, amino-coated, carboxyl-coated and encapsulated carboxyl group-coated paramagnetic microparticles.

In a particular embodiment, other functional groups can be coupled to the solid phase carriers through carboxyiimide coupling to carboxy groups on the sruface of the solid phase carrier. Solid phase carriers having a high density of carboxyl groups on the surface can be contacted with another functional group (e.g., oligo-dT) that binds to some but not all of the carboxy groups through carbodiimide coupling. Sufficient carboxy functional groups remain (which can be used, for example, to bind nucleic acid) following carboiimide coupling to a distinct functional group resulting in a solid phase carrier having dual functionality wherein binding of nucleic acid to the carboxy groups and a binding of a separate moiety to the second functional group can occur. Thus, the solid phase carriers can be used to remove or retain another target molecule.

Functional groups that bind target species, such as nucleic acids and peptides, are well known in the art (e.g., see Hermanson, G. T., *Bioconjugate Techniques*, Academic Press, San Diego, Calif. (1996) which is incorporated herein by reference). Functional groups that bind nucleic acid and peptides directly include, for example, metal ions, an amine group, a carboxyl group, an encapsulated carboxyl group, silica (SiOH), diethyl aminoethyl (DEAE), and a group which hybridizes to a nucleic acid sequence in the mixture.

A functional group which hybridizes to a nucleic acid sequence can be a nucleic acid sequence that is complementary to all or a portion of a nucleic acid in the mixture (e.g., complementary to all or a portion of the nucleic acid sequence of the target nucleic acid sequence to be isolated). In a particular embodiment, the nucleic acid sequence that is complementary is a sequence that is specific to (characteristic of) the nucleic acid species to be isolated so that substantially all the nucleic acid (the majority of nucleic acid species) in the mixture the bind the complementary sequence comprise the target nucleic acid species, while other nucleic acid sequences present in the mixture do not bind to the complementary sequence. For example, the group can be an oligodeoxythymidine (oligo dT) group which is a polymer of deoxyribothymidine and is complementary to the adenine nucleotide polymer (polyadenylate (polyA) tail) at the 3' end of messenger RNA (mRNA), and is a sequence that is characteristic of mRNA. Oligo dT groups can be a polymer of from about 3 to about 100 thymidines, from about 5 to about 75 thymidines, from about 8 to about 60 thymidines, from about 10 to about 50 thymidines, from about 15 to about 40 thymidines or from about 20 to about 30 thymidines. Modified oligo dT groups can also be used in the methods of the present invention. For example, an oligo dT wherein the last two 3' nucleotides are N or an oligo dT wherein the last two 3' nucleotides are VN, where "N" is adenine (A), cytosine (C), thymidine (T) or guanidine (G), and "V" is A, C or G can be used. In the method of isolating or separating globin RNA form nucleic acid present in a mixture, the functional group can be an oligonucleotide having a sequence complementary to all or a portion (a portion that distinguishes the sequence as a beta globin sequence) of the sequence of the beta globin being isolated.

In one embodiment, the functional group is a (one or more) transition metal ion which binds peptides (proteins) directly. For example, Immobilized Metal Ion Affinity Chromatography (IMAC) which was described by Porath et. al. (*Nature*, 258:598-599) is a well-known technique used for separation of proteins based on affinity between amino acid side chains and immobilized transition metal ions. Immobilized transition metals can form a reversible coordination complex with electron donor groups on the surface of proteins. In particular the side chains of histidine, cysteine, and tryptophan show affinity to transition metals including Cu, Zn, Co, and Ni. The metal ions are immobilized by way of metal chelators that are chemically coupled to an immobilized surface such as agarose, polyacrylimide, and silica. Common chelators include iminodiacetic acid (IDA), nitriloacetic acid (NTA), carboxymethyl aspartic acid (CM-Asp), and trsicarboxymethyl ethylene diamine (TED). Numerous others have been described (e.g., see U.S. Pat. Nos. 5,047,513 and U.S. 6,623,655; and US Published Application No. 2002/0019496 A1 which are incorpoated herein by reference). The complexes can be used to effectively separate proteins, which due to the reversible nature of the binding, can be eluted using non-denaturing or denaturing conditions. Though IMAC can be used to separate native proteins based on differing affinities to the metal complexes, the greatest commercial use has been through the introduction of a polyhistidine fusion tag to recombinant proteins and their subsequence purification via immobilized Ni complexes, generally IDA and NTA coupled to agarose (U.S. Pat. No. 5,284,933 and Schmitt et. al. Molecular Biology Reports, vol. 18, pp. 223-230, 1998, both of which are incorporated herein by reference). In addition, coupling of metal chelating complexes to microspheres (Lauer S A and Nolan J P. *Cytometry* 48:136-145, 2002) and water soluble polymers have also been described (U.S. Pat. No. 6,703,498, which is incorporated herein by reference).

In the methods of separating endotoxins from nucleic acid present in a mixture, the functional group can be PMXB, LALF, lipopolysaccharide binding protein (LBP), bactericidal/permeability-increasing protein (BPI), polymyxin and polymyxin analogs, amyloid P component, cationin protein, MD-2 and Toll-like receptor (TLR), CD14, Bac7, a synthetic peptide derived from a protein found in bovine neutrophils, *limulus* factor-C and synthetic peptides derived from Sushi3 domain thereof and antibodies raised against the lipid A component of endotoxin.

Groups that bind target species such as nucleic acid or peptides indirectly bind to a moiety, such as a label or tag, that is attached to the nucleic acid or peptide. Therefore, nucleic acid or peptides comprising a tag that can bind to a functional group on the solid phase carrier can be isolated using the methods of the present invention. Such groups include, for example, groups that interact with a binding partner. For example, the functional groups can be a binding partner which is conventionally used to isolate particular biomolecules based on their composition or sequence. Examples of such functional groups for use in the methods of the present invention include avidin, streptavidin, biotin, an antibody, an antigen, a sequence-specific interaction (a hybridizable tag), DNA specific binding protein (e.g., finger domains, transcription factors) and derivatives thereof.

In a particular embodiment, the functional group is biotin or a molecule that comprises biotin. Biotin, a water-soluble vitamin, is used extensively in biochemistry and molecular biology for a variety of purposes including macromolecular detection, purification and isolation, and in cytochemical staining (see, e.g., U.S. Pat. No. 5,948,624; the entire teachings of which are incorporated herein by reference). Biotin also has important applications in medicine in the areas of clinical diagnostic assays, tumor imaging and drug delivery, and is used extensively in the field of affinity cytochemistry for the selective labeling of cells, subcellular structures and proteins. The utility of biotin arises from its ability to bind strongly to the tetrameric protein avidin, found in egg white and the tissues of birds, reptiles and amphibians, or to its chemical cousin, streptavidin, which is slightly more specific for biotin than avidin. The biotin interaction with avidin is among the strongest non-covalent affinities known, exhibiting a dissociation constant of about $1.3 \times 10^{-15}$ M (Hermanson, G. T., *Bioconjugate Techniques*, Academic Press, San Diego, Calif. (1996), p. 570). In other embodiments, the functional group is biocytin and/or a biotin analog (e.g., biotin amido caproate-hydroxysuccinimide ester, biotin-$PEO_4$-N-hydroxysuccinimide ester, biotin 4-amidobenzoic acid, biotinamide caproyl hydrazide) and biotin derivatives (e.g., biotin-dextran, biotin-disulfide-N-hydroxysuccinimide ester, biotin-6 amido quinoline, biotin hydrazide, d-biotin-N hydroxysuccinimide ester, biotin maleimide, d-biotin p-nitrophenyl ester, biotinylated nucleotides, biotinylated amino acids such as N.epsilon.-biotinyl-1-lysine) (see, e.g., U.S. Pat. No. 5,948,624).

In another embodiment, the functional group is avidin or is a molecule that comprises avidin (avidinylated). Avidin is a glycoprotein found in egg whites that contains four identical subunits, each of which possesses a binding site for biotin (Hermanson, G. T., *Bioconjugate Techniques*, Academic Press, San Diego, Calif. (1996), p. 570). Streptavidin and other avidin analogs can also be used in the methods of the present invention. Such avidin analogs include, e.g., avidin conjugates, streptavidin conjugates, highly purified and/or fractionated species of avidin or streptavidin, non or partial amino acid variants of avidin or streptavidin (e.g., recombinant or chemically synthesized avidin analogs with amino acid or chemical substitutions which still allow for high affinity, multivalent or univalent binding of the avidin analog to biotin). Streptavidin is another biotin-binding protein that is isolated from *Streptomyces avidinii* (Hermanson, supra).

The functional group can also be an antibody. As used herein, the term "antibody" encompasses both polyclonal and monoclonal antibodies (e.g., IgG, IgM, IgA, IgD and IgE antibodies). The terms polyclonal and monoclonal refer to the degree of homogeneity of an antibody preparation, and are not intended to be limited to particular methods of production. Any antibody or antigen-binding fragment can be used in the methods of the invention. For example, single chain antibodies, chimeric antibodies, mammalian (e.g., human) antibodies, humanized antibodies, CDR-grafted antibodies (e.g., primatized antibodies), veneered antibodies, multivalent antibodies (e.g., bivalent) and bispecific antibodies are encompassed by the present invention and the term "antibody". Chimeric, CDR-grafted or veneered single chain antibodies, comprising portions derived from different species, are also encompassed by the present invention and the term "antibody". The various portions of these antibodies can be joined together chemically by conventional techniques, or can be prepared as a contiguous protein using genetic engineering techniques. For example, nucleic acids encoding a chimeric or humanized chain can be expressed to produce a contiguous protein. See, e.g., Cabilly et al., U.S. Pat. No. 4,816,567; Cabilly et al., European Patent No. 0,125,023 B1; Boss et al., U.S. Pat. No. 4,816,397; Boss et al., European Patent No. 0,120,694 B1; Neuberger, M. S. et al., WO 86/01533; Neuberger, M. S. et al., European Patent No. 0,194, 276 B1; Winter, U.S. Pat. No. 5,225,539; Winter, European Patent No. 0,239,400 B1; Queen et al., European Patent No. 0 451 216 B1; and Padlan, E. A. et al., EP 0 519 596 A1. See also, Newman, R. et al., *BioTechnology*, 10: 1455-1460 (1992), regarding primatized antibody, and Ladner et al., U.S. Pat. No. 4,946,778 and Bird, R. E. et al., *Science*, 242: 423-426 (1988)) regarding single chain antibodies.

Alternatively, the functional group can be an antigen. As used herein, the term "antigen", "immunogen" or "epitope" (e.g., T cell epitope, B cell epitope) refer to a substance for which an antibody or antigen-binding fragment has binding specificity. The antibodies and antigen-binding fragments for use in the methods of the invention have binding specificity for a variety of immunogens (e.g., polypeptides).

Any number of heterologous (distinct) functional groups (e.g., heterobifunctional, heterotrifunctional, heteromultifunctional) can be present on the surface of the solid phase particles as long as the presence of the functional groups do not interfere (e.g., chemically, sterically) with the reversible binding of the target species. In the methods of the present invention, at least two distinct functional groups are present on the solid phase carriers. In one embodiment, there can be a functional group from about every 2 $Å^2$ up to about 200 $Å^2$. In a particular embodiment, there is a functional group every 50.5 $Å^2$ on the solid phase carrier. In another embodiment, there is a functional group every 13.8 $Å^2$ on the solid phase carrier.

A person of skill in the art can envision any number of groups on the heteromultifunctional beads for use in the present invention. The number of distinct functional groups on a solid phase carrier can be from about 2 to about 100 distinct groups. In a particular embodiment, the solid phase carrier has two distinct functional groups (bifunctional solid phase carrier, such as bifunctional magnetic microparticles). In another embodiment, the solid phase carrier has two groups, one of which binds nucleic acid present in a mixture, and the other binds one or more non-nucleic acid components or moieties (e.g., endotoxin, an organism) present in the mixture. In yet another embodiment, the solid phase carrier has two groups, one of which binds al nucleic acid present in a mixture, and the other binds a particular target nucleic acid species (e.g., mRNA) present in the mixture.

In a particular embodiment, at least one of the functional groups is a streptavidin group or a derivative thereof.

In other embodiments, the solid phase carriers comprise two, distinct functional groups wherein the first functional group is a COOH group and the second functional group is a streptavidin group or derivative thereof; wherein the first functional group is a COOH group and the second functional group is an olig dT group or derivative thereof; first functional group is a COOH group and the second functional group is a PMXB group or derivative thereof; first functional group is a COOH group and the second functional group is a LALF group or derivative thereof; first functional group is a COOH group and the second functional group is a polyethyleneimine (PEI) group or derivative thereof; and first functional group is a COOH group and the second functional group is a poly-L-lysine (PLL) group or derivative thereof.

In the methods of the present invention, the combination of the mixture comprising the target species and the solid phase carriers are maintained under conditions appropriate for binding of the target species to the functional groups on the carriers. The methods and agents (reagents) described herein can be used together with a variety of purification techniques (e.g., nucleic acid and/or peptide purification techniques) which involve binding of nucleic acid to solid phase carriers, including those described in U.S. Pat. Nos. 5,705,628 (Hawkins); 5,898,071 (Hawkins); 6,534,262 (McKernan et al.), PCT Published Application No. WO 99/58664, U.S. Published Application No. 20020094519 A1, U.S. Pat. Nos. 5,047,513, U.S. 6,623,655 and U.S. Pat. No. 5,284,933 the contents of which are herein incorporated by reference.

As described herein, one or more agents (e.g., buffers, enzymes) are used to bind or remove the target species from the solid phase carriers. The components of the agents needed to bind and/or remove the target species from the solid phase carriers can be present in one agent or in multiple agents (e.g., a first agent, a second agent, a third agent, etc.). Accordingly, when more than one agent is used in the methods of the present invention, the agents can be used simultaneously or sequentially. Depending on the purpose for which the methods described herein are used, one of skill in the art can determine the number and order of agents to be used in the methods of the present invention.

In one embodiment, the agent is used in the methods of the present invention to cause the target species in the mixture to precipitate or absorb onto the functional groups on the surface of the solid phase carriers (a nucleic acid precipitating agent). In one embodiment, a nucleic acid or peptide precipitating agent is used at a sufficient concentration to precipitate the nucleic acid of the mixture onto the solid phase carrier.

A "nucleic acid precipitating reagent" or "nucleic acid precipitating agent" is a composition that causes the nucleic acid of a cell to go out of solution. Suitable precipitating agents include alcohols (e.g., short chain alcohols, such as ethanol or isopropanol) and a poly-OH compound (e.g., a polyalkylene glycol). The nucleic acid precipitating reagent can comprise one or more of these agents. The nucleic acid precipitating reagent is present in sufficient concentration to nonspecifically and reversibly bind the nucleic acid of the cell onto the solid phase carriers. Such nucleic acid precipitating agents can be used, for example, to bind nucleic acids non-specifically, or target nucleic acid species specifically, depending on the concentrations used, to solid phase carriers comprising COOH as a functional group.

In one embodiment, carboxy-based magnetic beads are used which involve binding nucleic acids to carboxyl coated solid phase carriers (e.g., magnetic microparticles) using various nucleic acid precipitating reagents (crowding reagents) such as alcohols, glycols (e.g., alkylene, polyalkylene glycol, ethylene, polyethylene glycol) and Polyvinyl Pyrrolidinone-40. The molecular weights of these crowding reagents can be optimized to produce low viscosity solutions with substantial precipitating power. Size specific nucleic acid isolation can be performed by either adjusting the concentration of the crowding reagent, the molecular weight of the crowding reagent or adjustment to salt, pH, polarity or hydrophobicity of the solution. Large nucleic acid molecules will be crowded out of solution at low concentrations of salt and crowding reagent whereas the smaller size species required higher concnetrations of crowding reagents. See, for example, U.S. Pat. No. 5,705,628; U.S. Pat. No. 5,898,071; U.S. Pat. No. 6,534,262 and U.S. Published Application No. 2002/0106686, all of which are incorporated herein by reference.

Suitable "peptide precipitating reagents" or "peptide precipitating agents" include any suitable affinity binding buffer (e.g,. U.S. Pat. Nos. 5,047,513; 6,623,655; 5,284,933; and US Published Application No. 2002/0019496, all of which are incorporated herein by reference).

Appropriate alcohol (e.g., ethanol, isopropanol) concentrations (final concentrations) for use in the methods of the present invention are from about 5% to about 100%; from about 40% to about 60%; from about 45% to about 55%; and from about 50% to about 54%.

Appropriate polyalkylene glycols include polyethylene glycol (PEG) and polypropylene glycol. Suitable PEG can be obtained from Sigma (Sigma Chemical Co., St. Louis Mo., Molecular weight 8000, Dnase and Rnase fee, Catalog number 25322-68-3) The molecular weight of the polyethylene glycol (PEG) can range from about 250 to about 10,000, from about 1000 to about 10,000, from about 2500 to about 10,000, from about 6000 to about 10,000, from about 6000 to about 8000, from about 7000 to about 9000, from about 8000 to about 10,000. In a particular embodiment PEG with a molecular weight of about 8000 is used. In general, the presence of PEG provides a hydrophobic solution which forces hydrophilic nucleic acid molecules out of solution. In one embodiment, the PEG concentration is from about 5% to about 20%. In other embodiments, the PEG concentration ranges from about 7% to about 18%; from about 9% to about 16%; and from about 10% to about 15%.

Optionally, salt may be added to the reagent to cause precipitation of the nucleic acid and/or peptide in the mixture onto the solid phase carriers. Suitable salts which are useful for facilitating the adsorption of nucleic acid molecules targeted for isolation to the magnetically responsive microparticles include sodium chloride (NaCl), lithium chloride (LiCl), barium chloride (BaCl$_2$), potassium (KCl), calcium chloride (CaCl$_2$), magnesium chloride (MgCl$_2$) and cesium chloride (CsCl). In one embodiment, sodium chloride is used. In general, the presence of salt functions to minimize the negative charge repulsion of the nucleic acid molecules. The wide range of salts suitable for use in the method indicates that many other salts can also be used and suitable levels can be empirically determined by one of ordinary skill in the art. The salt concentration can be from about 0.005M to about 5M, from about 0.1M to about 0.5M; from about 0.15M to about 0.4M; and from about 2M to about 4M.

Additional components may be added to the reagent. In one embodiment, RNAse is added to the nucleic acid precipitating agent.

In the embodiment in which the functional group is a sequence which is complementary, and thus hybridizes, to a nucleic acid species in the mixture, a hybridizing buffer can be used for binding. Suitable buffers for use in such a method are known to those of skill in the art. An example of a suitable buffer is a buffer comprising NaCl (e.g., about 01.M to about 0.5M), Tris-HCl (e.g., 10 mM), EDTA (e.g., 0.5 mM), sodium chcloride sodium citrate (SSC) and combinations thereof.

Depending on the functional group used (e.g., a streptavidin functional group which is used to bind a nucleic acid comprising a biotin label or tag), those of skill in the art will be able to determine the agent to use to either bind the nucleic acid and/or peptide to, or elute the nucleic acid and/or peptide from, the functional group on the solid phase carrier.

In the methods of the present invention, a mixture comprising a plurality of nucleic acids and/or peptide species are combined with solid phase carriers. Any mixture comprising a plurality of nucleic acids and or peptides can be used in the methods. Examples, of appropriate starting material include biological samples such as blood, tissue, tissue lysates, cells (intact or whole cells such as buccal cells), and cell lysates (cells in growth or culture media). Additional appropriate starting materials include assay samples comprising nucleic acid. Appropriate starting material also include cells obtained from either mammalian (i.e., human, primate, equine, canine, feline, bovine, murine) tissue or body fluids and lysates prepared from such cells. Examples of cells for use in the methods of the present invention include, but are not limited to, mammalian cells (e.g., blood cells, such as whole blood cells), bacterial cells (e.g., *E. Coli* such as DH5α, DH10B, DH12S, C600 or XL-1 Blue), yeast cells, plant cells, tissue cells (cells from, for example, *C. elegans*, mouse tails, human biopsies) and host cells containing exogenous nucleic acid (e.g., recombinant DNA, bacterial DNA or replicative form DNA) and/or peptides which are targeted for isolation from host cell chromosomal DNA and other host cell biomolecules. Alternatively, the starting material can be lysates prepared from such cells.

As used herein a "host cell" is any cell into which exogenous nucleic acid and/or peptide can be introduced, thereby producing a host cell which contains exogenous nucleic acid and/or peptide, in addition to host cell nucleic acid and peptides. As used herein the terms "host cell nucleic acid", "endogenous nucleic acid", "host cell peptides", and "endogenous peptides" refer to nucleic acid species (e.g., genomic or chromosomal nucleic acid) and peptide species that are present in a host cell as the cell is obtained. As used herein, the term "exogenous" refers to nucleic acid and peptides other than host cell nucleic acid (e.g., plasmid) and peptides; exogenous nucleic acid and peptides can be present into a host cell as a result of being introduced in the host cell or being introduced into an ancestor of the host cell. Thus, for example, a nucleic acid species (peptide species) which is non-endogenous, is not present in the host cell as it was obtained or an ancestor of the host cell. Appropriate host cells include, but are not limited to, bacterial cells, yeast cells, plant cells and mammalian cells.

As used herein, a "lysate" is a solution in which the cells' membranes have been disrupted by any means with the result that the contents of the cell, including the nucleic acid therein, are in solution. A "cleared lysate" is a lysate in which the chromosomal or genomic nucleic acid, proteins and membranes of the cell have been removed such as by chemical treatment or centrifugation of the lysate. Cells are lysed using known methods, thereby preparing a mixture suitable for use with the method of the instant invention. For example, cells can be lysed using chemical means (e.g., alkali or alkali and anionic detergent treatment, nonionic detergent (e.g., Triton X)), cationic detergent, isotonic shock, or physical disruption (e.g., homogenization).

The term "lysed host cell suspension", as used herein, refers to a suspension comprising host cells whose membranes have been disrupted by any means (e.g., chemical, such as alkali or alkali and anionic detergent treatment, nonionic detergent, cationic detergent, isotonic shock, or physical disruption by homogenization); such a suspension is a mixture of host cell biomolecules, cellular components and disrupted membrane debris. In one embodiment, a lysed host cell suspension suitable for use in the instant invention is prepared by contacting host cells with an alkali and anionic detergent (e.g., sodium dodecyl sulphate (SDS)) solution (e.g., 0.2 N NaOH, 1% SDS). Optionally, lysozyme could be included in the lysis buffer. The presence of an anionic detergent in the lysing solution functions to produce an anti-protein environment by neutralizing the effective charge of the proteins, thereby minimizing their attraction to the surfaces of the functional group-coated paramagnetic microparticles. In one embodiment, the lysed host cell suspension is non-neutralized.

According to the methods of the present invention, in one embodiment, a cell is combined with solid phase carriers and a reagent, wherein the reagent causes the nucleic acids of the cell to bind non-specifically and reversibly to the solid phase carriers. As described above, in the embodiment in which the starting material is a cell the agent(s) used in the methods of the present invention can be formulated to cause the lysis of a cell. A variety of lysis components can be used to cause the disruption of a membrane (such as alkali, alkali and anionic detergent treatment, or isotonic shock). In one embodiment, the lysis component of the reagent is an alkali (NaOH) and/or an anionic detergent (e.g., sodium dodecyl sulphate (SDS)) solution (e.g., final concentration of 0.2 N NaOH, 1% SDS when added to a cell). Optionally, lysozyme could be included in the lysis component of the first reagent. The presence of an anionic detergent in the lysis component functions to produce an anti-protein environment by neutralizing the effective charge of the proteins, thereby minimizing their attraction to the surfaces of the solid phase carrier (e.g., a functional group-coated paramagnetic microparticle). In one embodiment, an RNA lysis buffer is used. In a particular embodiment, the RNA lysis buffer is 20 mM Citrate buffer, pH 4.5, 2% sodium lauryl sarcosine, 10 mM EDTA, 1 mM Aurin tricarboxylic acid, 1% triton-x-100, 1M LiCl, 30% isopropanol, 0.05% sodium azide). In another embodiment, the RNA lysis buffer is 50 mM Citrate buffer, pH 7.0, 2% sodium lauryl sarcosine, 10 mM EDTA, 1 mM Aurin tricarboxylic acid, 1% triton-x-100, 1M LiCl, 30% isopropanol, 0.05% sodium azide According to the methods of the invention, the isolation of the target species in a mixture is accomplished by removing the nucleic acid-coated solid phase carrier from the combination. The solid phase carrier (e.g., a paramagnetic microparticle) can be recovered from the first combination, for example, by vacuum filtration, centrifugation, or by applying a magnetic field to draw down the solid phase carrier (e.g., a paramagnetic microparticle). Paramagnetic microparticles are preferably separated from solutions using magnetic means, such as applying a magnet field of at least 1000 Gauss. However, other methods known to those skilled in the art can be used to remove the magnetic microparticles from the supernatant (e.g., vacuum filtration or centrifugation). The remaining solution can then be removed, leaving solid phase carriers having the nucleic acid of the cell adsorbed to their surface.

As described herein agents which can be used to remove target species, such as nucleic acid and/or peptides, from the solid phase carriers include buffers, such as elution buffers. A suitable "elution buffer" for use in the methods of the present invention is a buffer that elutes (e.g., selectively) target species such as nucleic acid and/or peptides from the functional group(s) of the solid phase carriers. In one embodiment, a suitable elution buffer for use in the present invention can be water or any aqueous solution. For example, useful buffers include, but are not limited to, TRIS-HCl (e.g., 10 mM, pH 7.5), Tris acetate, sucrose (20%), EDTA and formamide (100%) solutions. In one embodiment, the elution buffer is a buffered salt solution comprising a monovalent (one or more) cation such as sodium, lithium, potassium, and/or ammonium (e.g., from about 0.1M to about 0.5M). Elution of nucleic acid or peptides from the solid phase carrier can occur quickly (e.g., in thirty seconds or less) when a suitable low ionic strength elution buffer is used. Once the bound target nucleic acid and/or peptide species have been eluted, the solid phase carrier, to which is bound non-target nucleic acid and/or peptide species, is separated from the elution buffer.

Optionally, the agent can comprise a component that degrades nucleic acid (e.g., an enzyme) or peptides (e.g., proteinases, such as proteinase K). For example, DNase (e.g., DNase I) can be added to degrade DNA (e.g., host cell DNA), thereby allowing RNA to bind to the solid phase carriers free, or essentially free of DNA. Alternatively, RNAse can be added to degrade RNA (e.g., host cell RNA), thereby allowing DNA to bind to the solid phase carriers free, or essentially free, from RNA. Alternatively, RNAse (e.g., 1.75 ng/ul RNAse/ddH$_2$O) can be added to the lysis component to degrade host cell RNA, thereby allowing DNA to bind to the solid phase carrier free, or essentially free, from RNA. The necessity of including a RNAse step will largely be determined by the size of the nucleic acid species that is targeted for isolation in the particular nucleic acid precipitation that is being performed. For example, if the conditions selected for isolation are appropriate for isolating nucleic acids comprising at least 4,000 base pairs, then it is unlikely that RNA species will be an appreciable contaminant.

In addition, impurities (e.g., host cell components, proteins, metabolites, chemicals or cellular debris) can be removed from the solid phase carriers by washing the solid phase carriers with target species bound thereto (e.g., by contacting the solid phase carriers with a suitable wash buffer solution) before separating the solid phase carrier-bound target species from the solid phase carriers. As used herein, a "wash buffer" is a composition that dissolves or removes impurities either bound directly to the microparticle, or associated with the adsorbed nucleic acid, but does not solubilize the target species absorbed onto the solid phase. The pH and solute composition and concentration of the wash buffer can be varied according to the types of impurities which are expected to be present. For example, ethanol (e.g., 70%) exemplifies a preferred wash buffer useful to remove excess PEG and salt. In one embodiment, the wash buffer comprises NaCl (e.g., 0.1M), Tris (e.g., 10 mM) and EDTA (e.g., 0.5 mM). The solid phase carriers with bound nucleic acid and/or peptide can also be washed with more than one wash buffer solution. The solid phase carriers can be washed as often as required (e.g., three to five times) to remove the desired impurities. However, the number of washings is preferably limited to in order to minimize loss of yield of the bound target species. A suitable wash buffer solution has several characteristics. First, the wash buffer solution must have a sufficiently high salt concentration (a sufficiently high ionic strength) that the nucleic acid and/or peptide bound to the solid phase carriers does not elute off of the solid phase carriers, but remains bound to the microparticles. A suitable salt concentrations is greater than about 0.1 M and is preferably about 0.5M. Second, the buffer solution is chosen so that impurities that are bound to the nucleic acid or microparticles are dissolved. The pH and solute composition and concentration of the buffer solution can be varied according to the types of impurities which are expected to be present. Suitable wash solutions include the following: 0.5×5 SSC; 100 mM ammonium sulfate, 400 mM Tris pH 9, 25 mM MgCl$_2$ and 1% bovine serum albumin (BSA); 1-4M guanidine hydrochloride (e.g., 1M guanidine HCL with 40% isopropanol and 1% Triton X100); and 0.5M NaCl. In one embodiment, the wash buffer solution comprises 25 mM Tris acetate (pH 7.8), 100 mM potassium acetate (KOAc), 10 mM magnesium acetate (Mg$_2$OAc), and 1 mM dithiothreital (DTT). In another embodiment, the wash solution comprises 2% SDS, 10% Tween and/or 10% Triton.

The components of the agents used in the methods of the present invention can be contained in a single agent (reagent) or as separate components. In the embodiment in which separate components of the agent(s) are used, the components can be combined simultaneously or sequentially with the mixture. Depending on the particular embodiment, the order in which the elements of the combination are combined may not necessarily be critical. The nature and quantity of the components contained in the reagent are as described in the methods above. The reagent may formulated in a concentrated form, such that dilution is required to obtain the functions and/or concentrations described in the methods herein.

The methods described herein can also be used to separate a duplex sequencing reaction into its respective forward and reverse Sanger extension products. Duplex sequencing reactions ensure impeccable read pairing and cut thermal cycler demand in half. For example, using bi-functional magnetic particles comprising streptavadin and carboxy functional groups, biotinylated forward reads can be bound to magnetic particles through biotin-streptavadin interaction while (simultaneously or subsequently) binding the reverse reads to carboxy functionalized beads in a reaction vessel (see FIG. 1). In a particular embodiment, biotinylated forward reads can be bound to magnetic particles through biotin-streptavadin interaction while subsequently binding the reverse reads to carboxy functionalized beads in a second reaction vessel. In this embodiment one standard streptavadin purification can be performed to capture most of the forward product which is eluted for sequencing with formamide. The supernatant is then moved to a new vessel and bifunctional streptavadin/carboxy beads are added followed by a two step binding reaction. Because the streptavadin/biotin interaction cannot be dissociated with water alone, the residual biotin labeled forward product remains on the bead mixture while the unlabelled reverse product is eluted from the carboxy groups and transferred to a new plate for capillary sequencing.

In another embodiment, the invention relates to a method of simultaneously or subsequently amplifying and sequencing a template DNA in the same reaction vessel using a biotinlylated forward primer and a reverse primer and separating the forward and reverse extension products. A template DNA, a biotinlylated forward primer, a reverse primer and a non-proofreading DNA polymerase are present in a polymerase chain reaction (PCR) comprising deoxynucleotide triphospahte (dNTP) (e.g., 2-10× concnetration) dependent upon the size of the amplicon, and labeled dideoxynucleotide triphosphate (ddNTP) terminators. In a particular embodiment, exponential amplification of the template occurs during the first few cycles of PCR. After a certain level of dNTP has been consumed, linear sequencing, consuming both dNTP's and labeled ddNTP's is the predominate reaction in the mixture producing forward and reverse extension products. Using bi-functional magnetic particles comprising streptavadin and carboxy functional groups, biotinylated forward reads can be bound to magnetic particles through biotin-streptavadin interaction while (simultaneously or subsequently) binding the reverse reads to carboxy functionalized beads in a reaction vessel. In a particular embodiment, biotinylated forward reads can be bound to magnetic particles through biotin-streptavadin interaction while subsequently binding the reverse reads to carboxy functionalized beads in a second reaction vessel. Streptavadin purification can be performed to capture most of the forward product which is eluted for sequencing with formamide. The supernatant is then moved to a new vessel and bifunctional streptavadin/carboxy beads are added followed by a two step binding reaction. Because the streptavadin/biotin interaction cannot be dissociated with water alone, the residual biotin labeled forward product remains on the bead mixture while the unlabelled reverse product is eluted from the carboxy groups.

Accordingly, the invention relates to a method of separating forward extension products and reverse extension products of a sequencing reaction. The method comprises combining a sequencing reaction mixture which comprises forward extension products and reverse extension products with solid phase carriers having a surface comprising a first functional group which selectively binds the forward extension products and a second functional group which binds nucleic acid, thereby producing a first combination. The first combination is maintained under conditions appropriate for binding of the forward extension products to the first functional group and binding of the reverse extension products to the second functional group. The solid phase carriers are removed from the first combination and combined with a buffer that selectively elutes the reverse extension products from the second functional group of the solid phase carriers, thereby producing a second combination. The solid phase carriers are removed from the second combination, thereby separating forward extension products and reverse extension products of the sequencing reaction.

In one embodiment of separating forward extension products and reverse extension products of a sequencing reaction, the method comprises combining a sequencing reaction mixture which comprises biotinylated forward extension products and reverse extension products with solid phase carriers having a surface comprising a (one or more) streptavidin functional group which selectively binds the forward extension products and a (one or more) COOH functional group which binds nucleic acid, thereby producing a first combination. The first combination is contacted with an agent that promotes binding of the biotinylated forwards to the streptavidin functional group (e.g., salt) and that promotes binding of nucleic acid to the COOH group (e.g., ethanol, polyethylene glycol).

Contacting the first combination with an agent that promotes binding of the biotinylated forwards to the streptavidin functional group and that promotes binding of nucleic acid to the COOH group, can be performed in one or more steps (e.g., one step, two steps, three steps, etc.) using one or more agents (e.g., a single agent, two agents, three ageents, etc.). In one embodiment, the first combination is contacted with a first agent that promotes binding of the biotinylated forwards to the streptavidin functional group (e.g., salt) and then contacted with a second agent that promotes binding of nucleic acid to the COOH group (e.g., ethanol, polyethylene glycol). In another embodiment, the first combination is contacted with a first agent that promotes binding of nucleic acid to the COOH group (e.g., ethanol, polyethylene glycol) and then contacted with a second agent that promotes binding of the biotinylated forwards to the streptavidin functional group (e.g., salt).

The solid phase carriers are removed from the first combination and combined with a buffer that selectively elutes the reverse extension products from the COOH functional group of the solid phase carriers (e.g., water), thereby producing a second combination. Alternatively, the solid phase carriers can be combined with a buffer that selectively elutes the forward extension products from the streptavidin group, thereby producing a second combination. The solid phase carriers are removed from the second combination, thereby separating forward extension products and reverse extension products of the sequencing reaction. This method can be also performed wherein the reverse extension products, rather than the forward extension products, are biotinylated.

In another embodiment of separating forward extension products and reverse extension products of a sequencing reaction, the method comprises combining a sequencing reaction mixture which comprises biotinylated forward extension products and reverse extension products with solid phase carriers having a surface comprising a (one or more) streptavidin functional group which selectively binds the forward extension products and a (one or more) COOH functional group which binds nucleic acid, thereby producing a first combination. The first combination is contacted with an agent that promotes binding of the biotinylated forwards to the streptavidin functional group (e.g., salt) and that promotes binding of nucleic acid to the COOH group (e.g., ethanol, polyethylene glycol). This step can be performed in one or more steps (e.g., one step, two steps) using one or more agents (e.g., a single agent, two agents). The solid phase carriers are removed from the first combination and combined with a buffer that selectively elutes the reverse extension products from the COOH functional group of the solid phase carriers (e.g., water), thereby producing a second combination. Alternatively, the solid phase carriers can be combined with a buffer that selectively elutes the forward extension products from the streptavidin group, thereby producing a second combination. The solid phase carriers are removed from the second combination, thereby separating forward extension products and reverse extension products of the sequencing reaction. This method can be also performed wherein the reverse extension products, rather than the forward extension products, are biotinylated.

In a particular embodiment, the present invention relates to a method of separating forward extension products and reverse extension products of a sequencing reaction. In this embodiment, the method comprised combining a sequencing reaction mixture which comprises forward extension products and reverse extension products with solid phase carriers having a surface comprising a first functional group which selectively binds the forward extension products and a second functional group which binds nucleic acid, thereby producing a first combination. The first combination is maintained under conditions appropriate for binding of the forward extension products to the first functional group. The solid phase carriers are removed from the first combination thereby producing a second mixture comprising the reverse extension products. The solid phase carriers are combined with a buffer (e.g., formamide) that selectively elutes the forward extension products from the first functional group of the solid phase carriers, thereby producing a second combination. The solid phase carriers are separated from the second combination and combined with the second mixture, thereby producing a third combination. The third combination is maintained under conditions appropriate for binding of the reverse extension products to the second functional group. The solid phase carriers are removed from the third combination and combined with a buffer that selectively elutes the reverse extension products from the second functional group of the solid phase carriers, thereby separating forward extension products and reverse extension products of the sequencing reaction.

In another embodiment, the methods described herein can also be used to separate a nucleic acid species and a peptide species. For example, using bifunctional magnetic beads comprising carboxy and immobilized metal ion functional groups, DNA or RNA can be bound to the particles via interaction with carboxy groups while, simultaneously or subsequently, peptides can be bound to the particles via interaction with immobilized metal ion complexes. In one particular embodiment, cells recombinantly expressing a polyhistidine fusion protein can be lysed and both the recombinant protein and recombinant DNA species which expresses the recombinant protein can be bound and isolated by the bifunctional microparticles. Such a technique is useful for isolating protein and the recombinant DNA clone that expresses the protein in the iterative process of directed evolution or in screening expression constructs from a cDNA library. In another embodiment, mRNA and protein can be isolated by bi-fuctional beads containing carboxy or oligo-dT functional groups to bind mRNA and immobilized metal ion functional groups to bind protein. Such a technique is useful for co-purifying protein and mRNA for quantitative co-assessment of gene transctiptional and translational expression levels for proteomic applications.

In the methods of the present invention, the isolated target species can be subjected to further analysis, such as sequence analysis (e.g., by polyacrylamide gel or capillary electrophoresis). Nucleic acids isolated by the disclosed method can be used for molecular biology applications requiring high quality nucleic acids (e.g., the preparation of DNA sequencing templates; the microinjection, transfection or transformation of mammalian cells; the in vitro synthesis of RNA probes; reverse transcription cloning; cDNA library construction; PCR amplification; or gene therapy research; as well as for other applications with less stringent quality requirements including, but not limited to, transformation; restriction endonuclease or microarray analysis; selective RNA precipitations; in vitro transposition; separation of multiplex PCR amplification products; in vitro siRNA; RNAi hairpins; preparation of DNA probes and primers and detemplating protocols).

The isolation of high quality nucleic acid preparations from starting solutions of diverse composition and complexity is a fundamental technique in molecular biology. Thus, as a result of the work described herein, novel and readily automatable methods of separating nucleic acid molecules are now available. In one embodiment, the reagent is added to the cell by a multisample transfer device. In another embodiment, the first reagent is added simultaneously to a plurality of samples, e.g., at least 6, 12, 24, 96, 384, or 1536 samples, each sample containing one or more cells. In another embodiment, the first reagent is sequentially delivered to a plurality of samples (e.g. at least 6, 12, 24, 96, 384, or 1536 samples) each sample containing, for example, one or more cells. The invention includes methods of analyzing a plurality of nucleic acid samples. The methods include providing a plurality of nucleic acid samples isolated by a method described herein and analyzing the samples, e.g., performing sequence analysis on the samples.

The present invention is also directed to kits for use in the methods of the present invention. In one embodiment, the kit comprises heteromultifunctional (heterobifunctional) solid phase carriers and a cell lysis buffer. The kits of the present invention can further comprise additional buffers (e.g., lysis buffers, wash buffers and elution buffers) enzymes for nucleic acid degradation and instructions for use. In particular embodiments, the kit comprises bifunctional magnetic microparticles comprising COOH groups and oligo dT groups, and optionally, a cell lysis buffer; bifunctional magnetic microparticles comprising COOH groups and streptavidin groups; bifunctional magnetic microparticles comprising a COOH group and an olig dT group or derivative thereof; bifunctional magnetic microparticles comprising a COOH group and a PMXB group or derivative thereof; bifunctional magnetic microparticles comprising a COOH group and a LALF group or derivative thereof; bifunctional magnetic microparticles comprising a COOH group and a polyethyleneimine (PEI) group or derivative thereof; and bifunctional magnetic microparticles comprising a COOH group and a poly-L-lysine (PLL) group or derivative thereof.

EXAMPLE 1

Separation of Duplex Sequencing Reactions Using Two Functional Groups on Magnetic Beads Methods/Materials A mixture containing the following reagents and amounts per reaction was made.

| Reagent | Amount, ul | Concentration in reaction |
|---|---|---|
| BigDye terminator sequencing mix v2 | 1 | ⅛x |
| Biotin-M13 forward primer | 0.04 | 0.2 umol |
| M13 reverse primer | 0.025 | 1.0 umol |
| pGEM template DNA | 0.7 | 140 ng |
| water | 3.255 | |
| Total | 5 | |

The mixture was placed mixture in 96 well thermocycling plate and cycled sequenced using the following parameters:

| | |
|---|---|
| Step 1. | 95° C. for 10 s |
| Step 2. | 50° C. for 5 s |
| Step 3. | 60° C. for 150 s |
| Step 4. | Repeat steps 1-3 40 times |
| Step 5. | 4° C. hold |

Procedure A. Streptavidin Magnetic Bead Cleanup (Forward Sequence)

1. To the 5 uL sequencing reaction there was added 2.5 uL of magnetic streptavadin beads and 7.5 uL of 5M NaCl and the reaction was mixed well.
2. The magnetic beads containing the bound biotin-forward sequencing fragments were separated from solution by placing on a magnet plate for 5 mins.
3. The supernatant containing reverse sequencing fragments was aspirated and dispensed into a new well for reverse sequence clean-up (Procedure B).
4. Washed strepavidin beads 2× with 40 uL ddH2O, resuspending beads during each wash.
5. Resuspended beads in 20 uL Hi-Dye formamide, spun down, and incubated at 90° C. for 10 minutes to elute the forward sequencing fragments.

Procedure B. Carboxyl Bead Cleanup of Supernatant (Reverse Sequence):
1. Added 5 uL of diluted carboxyl coated magnetic beads and 23 uL 85% ethanol per well to the supernatant sample from Step 3, Procedure A and mixed well.
2. The magnetic beads containing the bound reverse sequencing fragments were separated from solution by placing on a magnet plate for 5 minutes.
3. Aspirated and discard supernatant.
4. Washed beads 2× with 40 uL 85% ethanol.
5. Resuspended beads in 20 uL ddH2O to elute the reverse sequencing fragments.

Forward and reverse sequencing fragments were analyzed, separately, on an ABI 3700.

Figure 2:
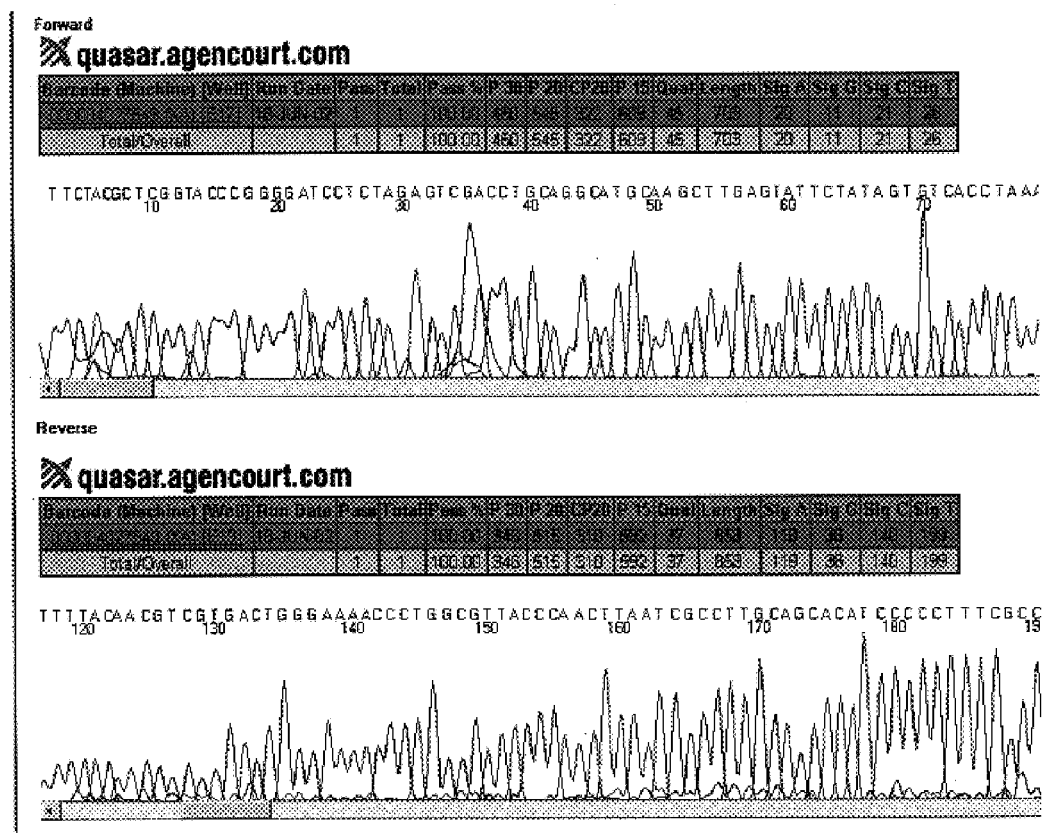
FIG. 2 shows the sequencing results of a duplex sequencing reaction using the solid phase based purification procedure. The sequence presented in the top panel (Forward) is SEQ ID NO 1 and the sequence presented in the bottom panel (Reverse) is SEQ ID NO 2.

Results/Discussion:

Successful separation and sequencing of the two fragment populations is demonstrated using magnetic beads with two different functional groups. See FIG. 1. Analysis of both the forward and reverse sequencing reactions is shown in FIG. 2. An effective separation of the forward and reverse sequencing fragments from the same reaction is demonstrated by a clean signal indicated by the Phred 20 quality scores (P20).

EXAMPLE 2

Isolation of Total RNA Using Bi-Functional Oligo-dT/Carboxyl Beads

To Test Oligo-dT Modified Carboxyl Beads for the Ability to Perform SPRI Purification of Total RNA.

Procedure

Started with 1.75×10e7 293T cells pelleted in 15 ml conical tubes. Resuspended the two pellets in 3 mls RNA lysis buffer (20 mM Citrate buffer, pH 4.5, 2% sodium lauryl sarcosine, 10 mM EDTA, 1 mM Aurin tricarboxylic acid, 1% triton-x-100, 1M LiCl, 30% isopropanol, 0.05% sodium azide, 0.03% magnetic carboxyl or oligo-dT magnetic beads) in a 15 ml conical. Put on magnet for 15 minutes. Beads were washed by resuspending in 5 mls 4 M Guanidine-HCL/40% Isopropanol buffer then placing on magnet. Second and third washes were with 1 ml 90% ethanol. The beads were transferred to 1.5 ml eppendorf tube. Wash 4 and 5 were also with 1 ml 90% ethanol. Let the beads dry and eluted with 100 uL DEPC water. Pelleted in microcentrifuge and recovered 45 uL.

Results

Figure 3:
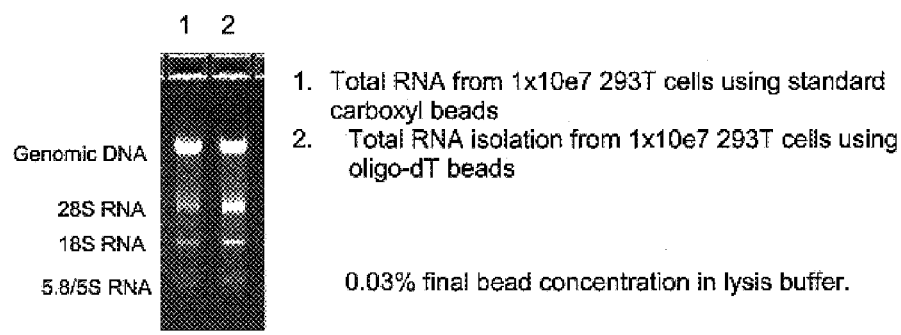
FIG. 3 is a gel showing that both carboxyl beads and bi-functional oligo-dT carboxyl beads are able to isolate genomic DNA and total RNA via the solid phase reversible immobilization (SPRI) technique.

The bi-functional oligo-dT/carboxyl beads are able to function in the SPRI process to isolate both genomic DNA and total RNA as indicated by comparison to the same isolation performed with the standard carboxyl beads. The gel in FIG. 3 shows total RNA 28, 18 and 5.8/5S ribosomal bands and genomic DNA bands. Both standard carboxyl beads and bi-functional oligo-dT/carboxyl beads give approximately equivalent yields of RNA as determined by Ribogreen analysis of the samples.

Quantitated with RiboGreen—

|  | ng/ul | Total amount of RNA, ug |
| --- | --- | --- |
| Oilgo-dT bead total RNA Purification | 403.8 | 18.2 |
| Carboxyl bead total RNA Purification | 391.5 | 17.6 |

EXAMPLE 3

Direct mRNA Isolation from Cells

Direct Isolation of mRNA from $1 \times 10^6$ 3638C Cells Using Bi-Functional Oligo-dT/Carboxyl Beads.

Procedure:
1. Had $1.1 \times 10^7$ 3638C cells frozen in −80° C. Thawed and resuspended in 10 mls total 100 mM NaCl, 10 mM Tris to give about $1 \times 10^6$ cells per ml.
2. Pelleted 2×1 ml cells in epi tubes at 14K×g, RT.
3. Resuspended pellets in either 0.5 mls RNA Lysis buffer pH 7.0 with 0.03% bi-functional oligo-dT beads or std carboxyl beads.
4. Incubated at RT 5 minutes.
5. Incubated on magnet for 5 minutes.
6. Resuspended each pellet in 0.5 mls Wash Buffer pH 7.3 (1M G-HCl, 1% TX-100, 25 mM NaCitrate, 30% iso)
7. Placed on magnet 5 minutes.
8. Washed pellets ×4 with 70% ethanol, 500 uL each, 30 sec. Let dry for 5 minutes. At this point, the beads have total nucleic acid bound to them.
9. To preferentially isolate the mRNA, the beads were resuspended in 160 uL 65° C. 1× hybridization buffer (0.5M NaCl, 10 mM Tris-HCl, pH 7.5, 0.5 mM EDTA). Let cool at room temperature for 5 minutes, placed on magnet 2 minutes, then repeated the resuspension in 160 uL 65 C 1×Hyb buffer and cooled at room temperature 5 minutes. Placed on magnet 2 minutes
10. Resuspended beads in 160 uL hybridization buffer, placed on magnet for 2 minutes.
11. Resuspended beads in 80 uL Wash Buffer (0.1M NaCl, 10 mM Tris-HCl, pH 7.5, 0.5 mM EDTA), moved to a fresh tube and placed on magnet for 2 minutes.
12. Resuspended beads in 20 uL 65 C DEPC RNAse free water, placed on magnet 2 minutes, then moved to fresh tube. Stored at −20° C.

Results

Figure 4:
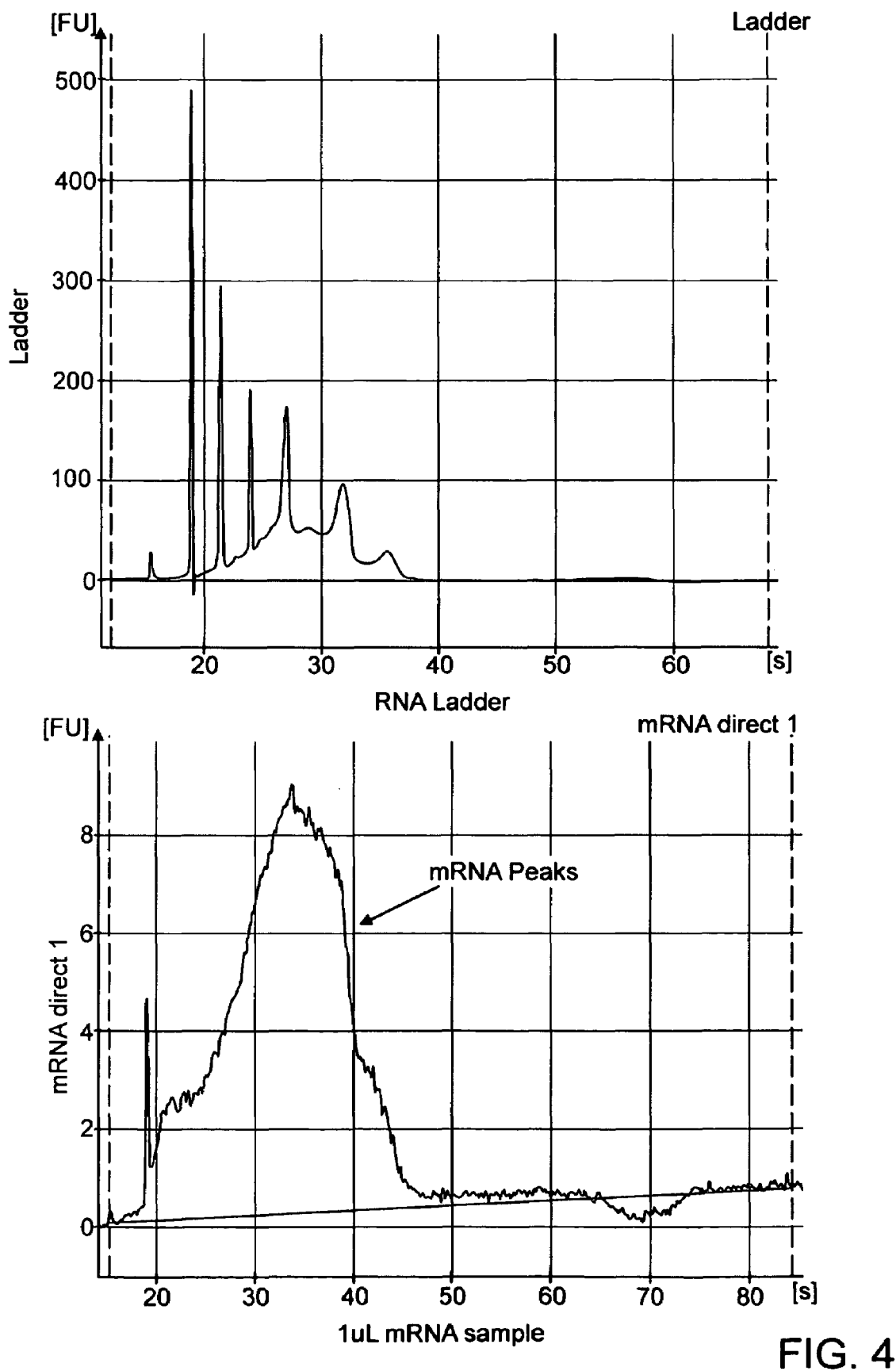
FIG. 4 show graphs of experimental data which illustrate mRNA isolation from cells.

Ran 1 uL on a Bioanalyer 2100 using a Pico RNA chip. The top electropherogram in FIG. 4 shows the RNA ladder. The bottom electropherogram in FIG. 4 shows a typical mRNA profile with a range of mRNA size fragments that show up as a broad peak indicating successful isolation of mRNA with the bi-functional oligo-dT/carboxyl beads.

EXAMPLE 4

Direct mRNA Isolation from Cells

Purpose

Direct Isolation of mRNA from $5 \times 10^5$ 3638C cells using bi-functional oligo-dT/carboxyl beads and standard carboxyl beads.

Procedure
1. Had $9.9 \times 10^6$ 3638 C cells frozen in −80° C. Thawed and resuspended in 10 mls total 100 mM NaCl, 10 mM Tris to give about 1×10e6 cells per ml.
2. Pelleted 2×0.5 ml cells in eppendorf tubes at 14 K×g, RT.
3. Resuspended pellets in either 0.5 mls RNA Lysis buffer pH 7.0 with 0.03% oligo-dT/carboxyl beads or std carboxyl beads.
4. Incubated at RT 5 minutes.
5. Incubated on magnet for 5 minutes.

6. Removed supernatant and resuspended each pellet in 0.5 mls Wash Buffer pH 7.3 (1M G-HCl, 1% TX-100, 25 mM NaCitrate, 30% iso)
7. Placed on magnet 5 minutes.
8. Washed pellets ×4 with 70% ethanol, 500 uL each, 30 sec. Let dry for 5 minutes. At this point, the beads have total nucleic acid bound to them.
9. To preferentially isolate the mRNA, the beads were resuspended in 80 uL 65° C. 1× hybridization buffer (0.5M NaCl, 10 mM Tris-HCl, pH 7.5, 0.5 mM EDTA). Let cool at room temperature for 5 minutes, placed on magnet 2 minutes, then repeated the resuspension in 80 uL 65° C. hybridization buffer and cooled at room temperature 5 minutes. Placed on magnet 2 minutes.
10. Resuspended beads in 40 uL Wash Buffer (0.1M NaCl, 10 mM Tris-HCl, pH 7.5, 0.5 mM EDTA) moved to a fresh tube and placed on magnet for 2 minutes.
11. Resuspended beads in 10 uL 65° C. water, placed on magnet 2 minutes, then moved to fresh tube. Stored at −20° C.

Results

Figure 5:
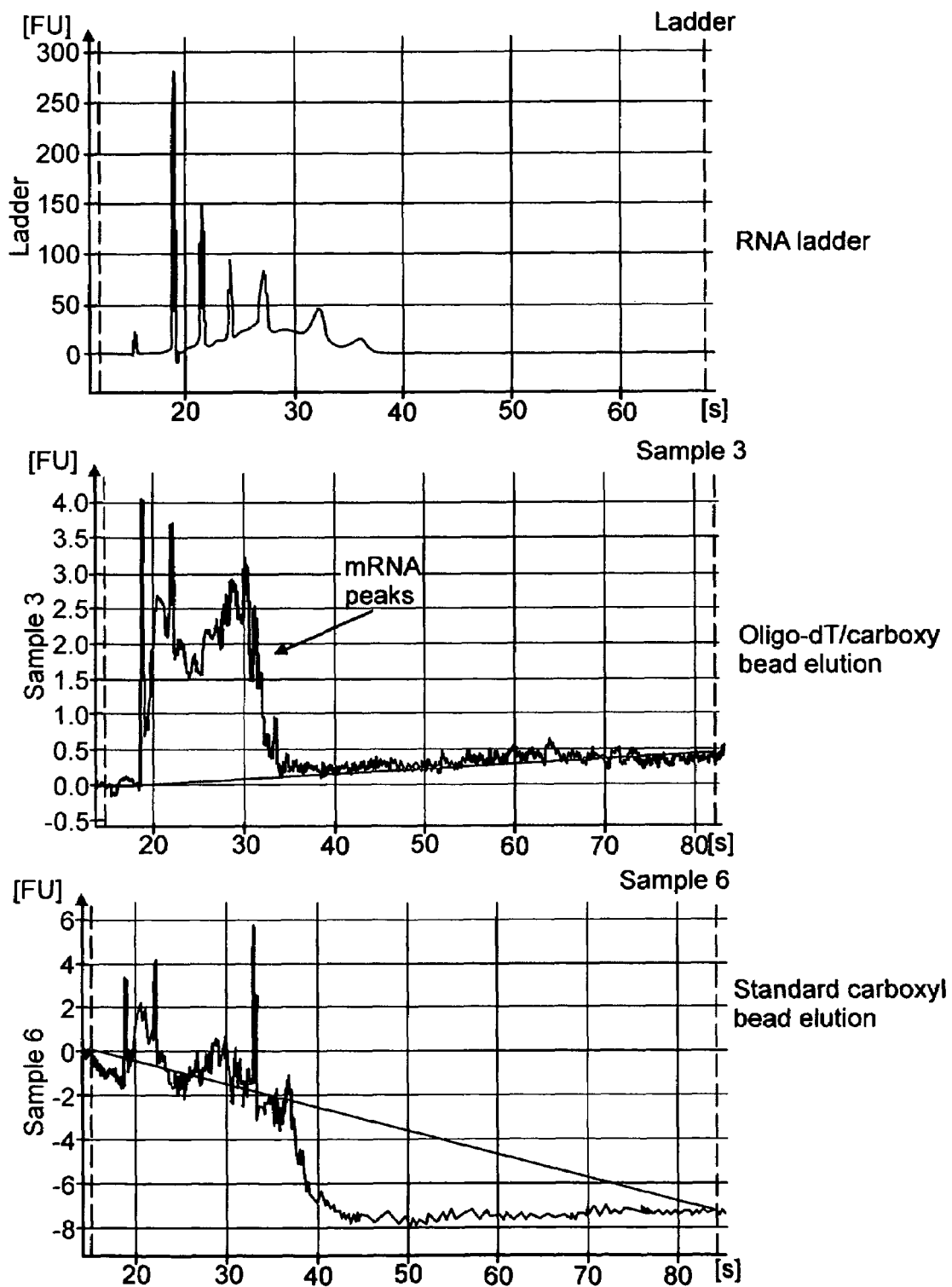
FIG. 5 shows three graphs of experimental data which illustrate mRNA isolation from cells.
Figure 6:
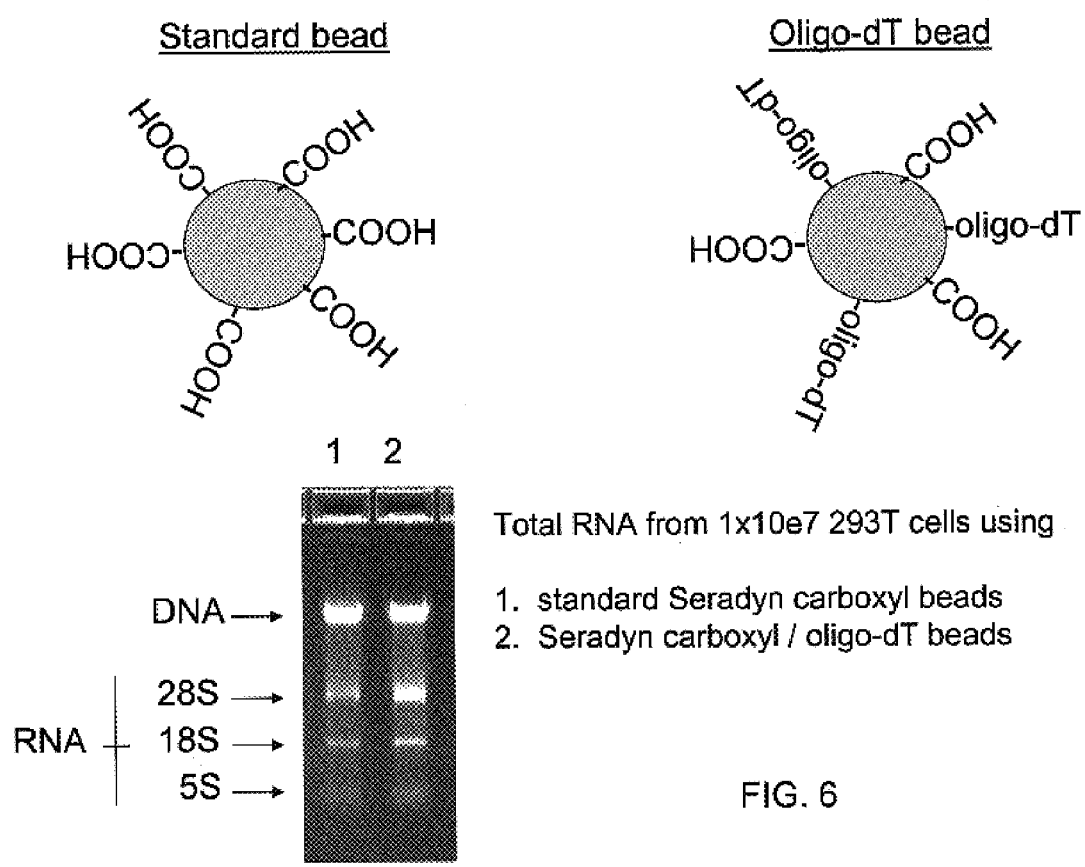
FIG. 6 is a schematic of the standard carboxyl bead and the oligo-dT bead.
Figure 7:
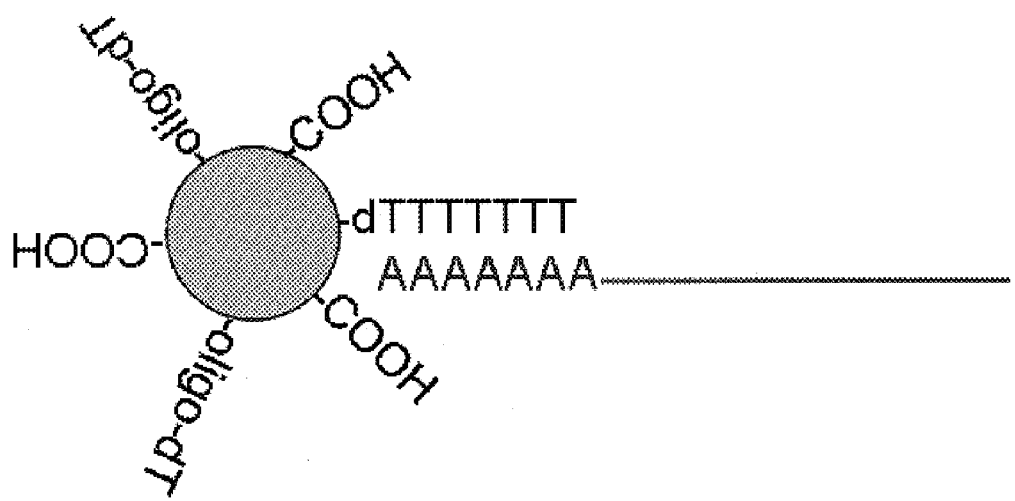
FIG. 7 is a schematic showing poly-A RNA hybridized to the oligo-dT bead.
Figure 8:
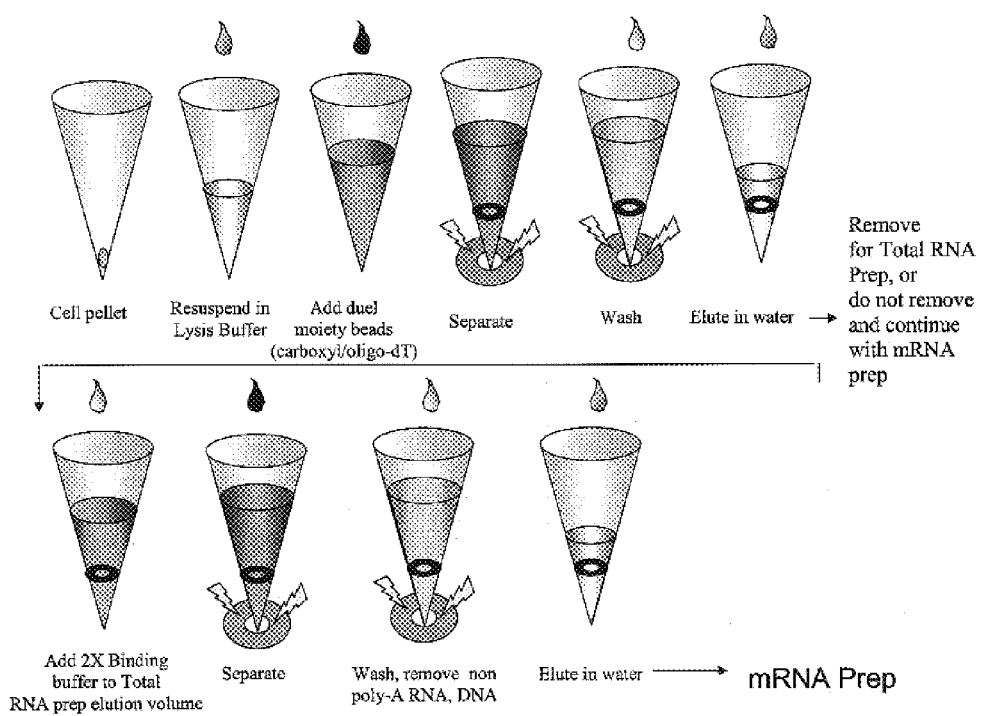
FIG. 8 is a schematic of direct mRNA preparation.

Ran 1 uL of each on a Bioanalyer 2100 using a Pico RNA chip. The top electropherogram in FIG. 5 shows the RNA ladder. The middle shows successful isolation of mRNA with oligo-dT/carboxyl beads as indicated by the broad peak. The bottom electropherogram indicates that the standard carboxyl beads do not isolate mRNA as indicated by the absence of a mRNA peak.

EXAMPLE 5

Adsorption of Polymyxin-B with Carboxy Beads

Since PXMB carries a net positive charge at pH<10, it should associate readily with carboxy beads. In the next experiment, we investigated the adsorption of PMXB onto carboxy beads for preparation of an endotoxin removal reagent.

Figure 9:
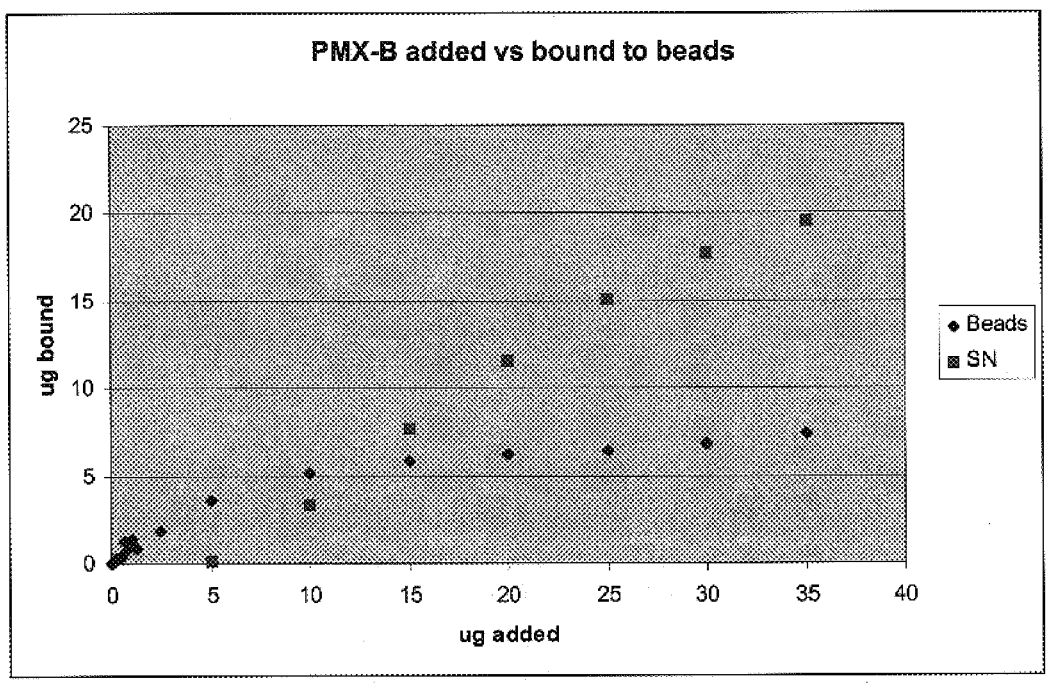
FIG. 9 is a graph showing PMX-B added to solution versus PMX-B bound to beads.

Procedure: Protein can be adsorbed onto carboxy beads easily in the presence of MES buffer at pH 6.1 using standard procedures (Seradyn Microparticle Reagent Optimization Manual). The association is due to both charge and hydrophobicity interactions. The amount of protein that can be loaded onto the carboxy beads is determined empirically for each protein. To determine the maximal level of PMXB adsorption, increasing amounts of PMXB were added to a 1% carboxy bead solution in 25 mM MES buffer pH 6.1 and mixed gently on a rotating platform for 24 hours. The amount of bound and unbound protein was determined by BCA assay as described above. To determine the optimal amount of carboxy beads required, a similar titration experiment was performed with carboxy bead concentrations as the variable. Results: Ten micrograms of PMXB was sufficient to saturate a 0.1 ml solution of 1% carboxy beads, with the remainder of the protein being found in the supernatant (SN) (FIG. 9)

EXAMPLE 6

Endotoxin Removal Using Bi-functional Beads

Endotoxin Free DNA Preparation with Bi-Functional Beads Made by Adsorption of Polymyxin-B to Magnetic Beads.

Figure 10:
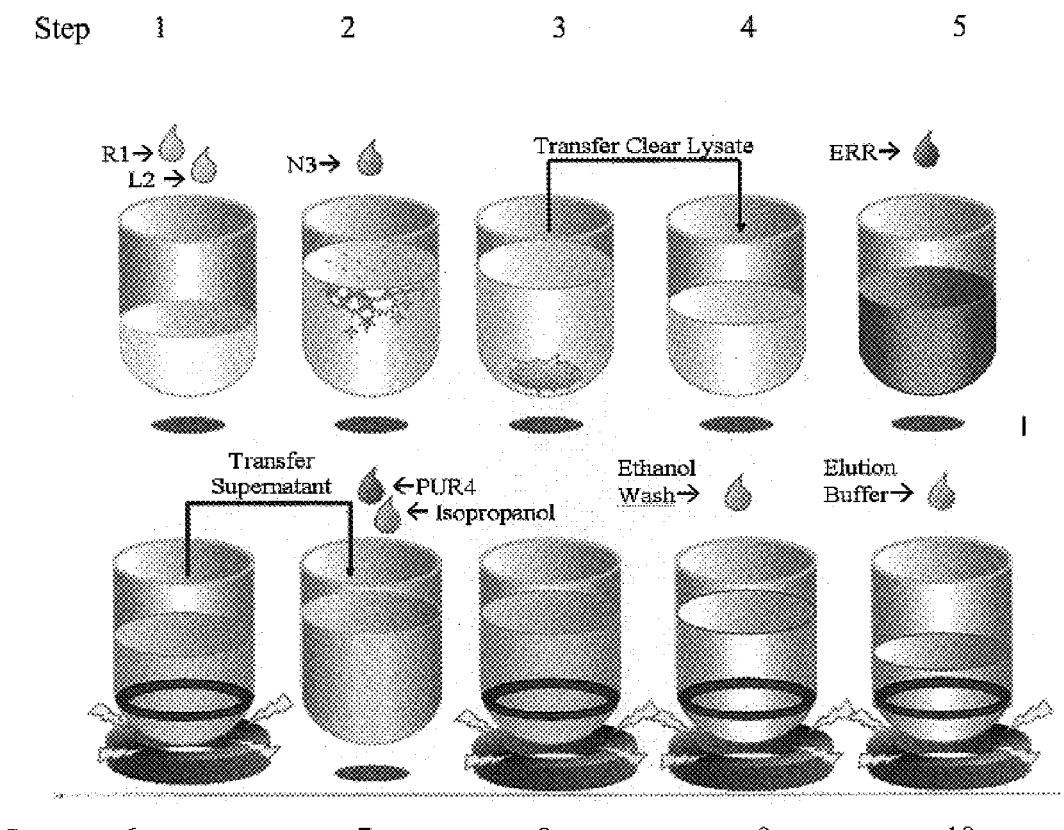
FIG. 10 is a schematic of endotoxin removal from a plasmid preparation.

An endotoxin removal reagent (ERR) consisting of polymyxin-B (PMXB) adsorbed onto carboxy modified (CM) beads was prepared as follows: 0.1 mg/mL PMXB dissolved in 25 mM MES buffer (pH 6.1) and mixed with CM beads (1% final). The solution was equilibrated for a minimum of 24 hours on a roller platform at 4 C. The ERR reagent was tested for the ability to remove endotoxin from plasmid preparations in conjunction with Agencourt's CosMcPrep DNA purification kit as illustrated in FIG. 10. Briefly, to each 240 uL of cleared lysate (FIG. 10, step 4), 100 uL ERR was added (containing 10 ug PMXB). Following incubation and magnetic removal of the ERR beads, plasmid DNA in the supernatant was purified via SPRI (FIG. 10, steps 7-10).

The amount of endotoxin in plasmid DNA preparations was determined by a photometric *Limulus* Amoebocyte Lysate (LAL) assay from BioWhittaker. This assay conforms to the United States Food and Drug Administration published guidelines for establishing endotoxin limits for pharmaceuticals and medical devices and for validating the use of LAL as an end-product endotoxin test.

FIG. 10 shows CosMcPrep (Agencourt) DNA purification kit modified to contain an endotoxin removal step.

Several reagents were tested for removal of endotoxin from the cleared lysate in addition to the ERR reagent. These included Magnesil silica magnetic beads (Promega), CM beads, PMXB agarose (Pharmacia), CM beads mixed with PMXB (PMXB+CM beads non-absorbed), and CM beads with PMXB adsorbed (PMXB/CM beads, aka ERR reagent). The various bead reagents were mixed with cleared lysate for one hour before proceeding to SPRI purification of the plasmid DNA. Endotoxin levels were determined by the LAL assay. All results were normalized to the amount of endotoxin per milligram DNA found in untreated controls.

Results

Figure 11:
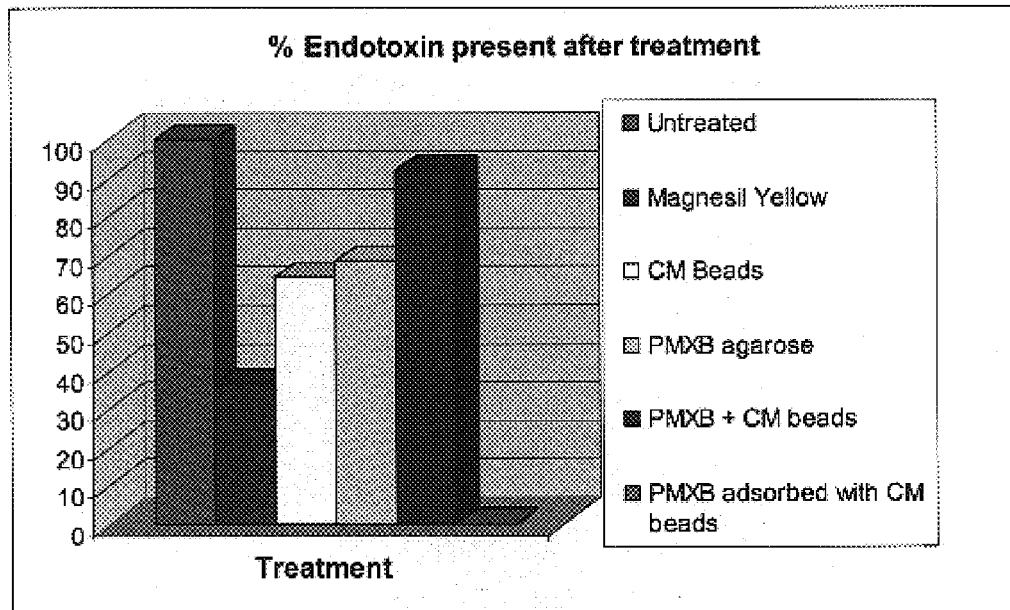
FIG. 11 is a bar graph showing endotoxin removal with adsorbed PMXB/CM beads.
Figure 12:
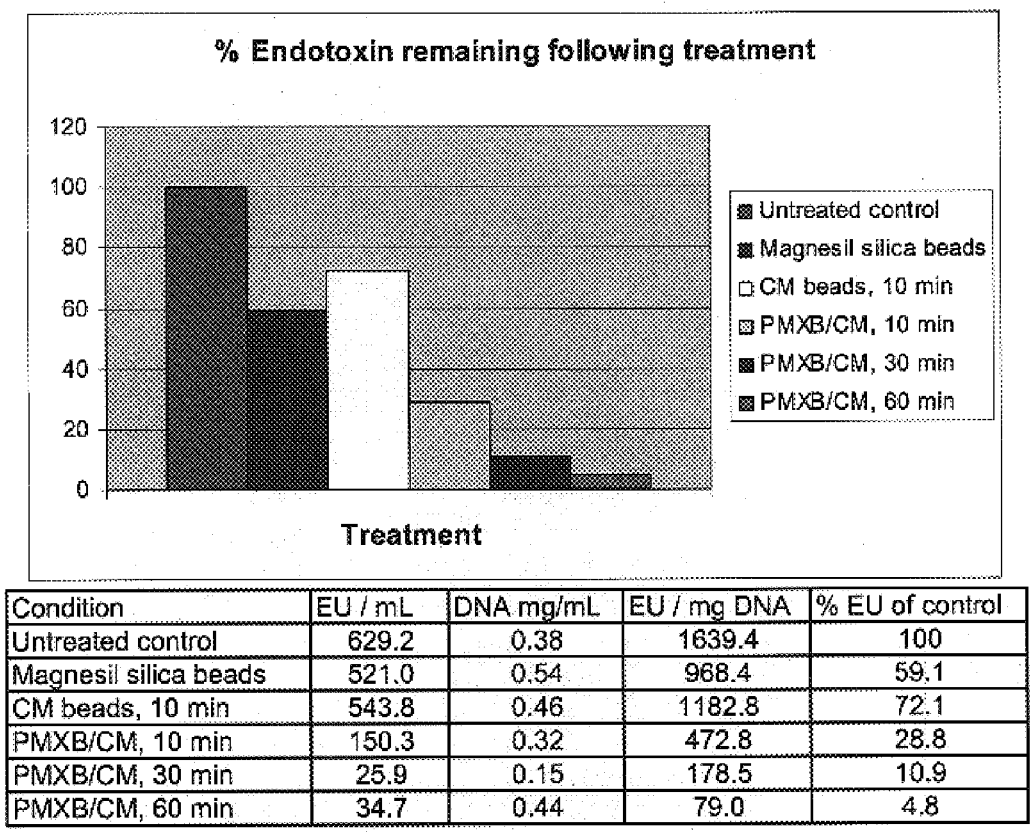
FIG. 12 is a bar graph showing endotoxin removal with PMXB/CM beads as a function of time.

FIG. 11 shows that PMXB absorbed to CM beads were found to be an effective reagent for removal of endotoxin from plasmid DNA preparations, with less than 1% of the amount of endotoxin remaining in the plasmid DNA in this experiment compared to control. Silica coated magnetic beads were intermediate in effectiveness while CM beads alone or PMXB-agarose beads were much less effective. The endotoxin removal was found to depend upon adsorption of the PMXB to the CM beads, as CM beads with PMXB added, but not adsorbed, was not effective in removing the endotoxin. Endotoxin removal was also proportional to the duration of exposure to the PMXB/CM beads, as summarized in FIG. 12. In this experiment, after 30 minutes incubation of the cleared lysate with ERR solution, the amount of endotoxin present in the plasmid DNA was significantly less than 300 EU/mg DNA required for therapeutic use. FIG. 10 shows endotoxin removal with adsorbed PMXB/CM beads. FIG. 12 shows endotoxin removal with PMXB/CM beads as a function of time.

| Condition | EU/mL | DNA mg/ml | EU/mg DNA | % EU of Control |
|---|---|---|---|---|
| Untreated | 628.2 | 0.2 | 2886.5 | 100.0 |
| Magnesil Silica | 550.9 | 0.5 | 1055.2 | 36.6 |
| CM Beads | 633.0 | 0.3 | 1857.7 | 64.4 |
| PMXB-agarose | 621.5 | 0.3 | 1979.1 | 68.6 |
| PMXB + CM beads | 612.7 | 0.2 | 2659.4 | 92.1 |
| PMXB/CM beads | 0.5 | 0.1 | 3.6 | 0.1 |

| Condition | EU/mL | DNA mg/ml | EU/mg DNA | % EU of Control |
|---|---|---|---|---|
| Untreated Control | 629.2 | 0.38 | 1639.4 | 100 |
| Magnesil silica beads | 521.0 | 0.54 | 968.4 | 59.1 |
| CM Beads, 10 min | 543.8 | 0.46 | 1182.8 | 72.1 |
| PMXB/CM, 10 min | 150.3 | 0.32 | 472.8 | 28.8 |
| PMXB/CM, 30 min | 25.9 | 0.15 | 178.5 | 10.9 |
| PMXB/CM, 60 min | 34.7 | 0.44 | 79.0 | 4.8 |

EXAMPLE 7

Endotoxin Free DNA Preparation with Bi-Functional Beads Made by Adsorption of Limulus Anti-LPS Factor to Magnetic Beads PMXB has several advantages, including low cost and availability in large quantities, but other endotoxin binding proteins can be used in the method as well. Procedure: Three preparations of the Limulus anti-LPS factor (LALF) isolated from the American Horseshoe crab (Limulus polyphemus) were examined for this purpose. The three preparations include the LALF native protein isolate (Lp), a recombinant LALF expressed in Pichia pastoris (Pp), and a recombinant LALF expressed in Saccharomyces cerevisiae (Sc). The three proteins differ in their ability to neutralize endotoxin in an in vitro assay (Sc>Pp>Lp). The proteins were absorbed onto CM beads as described for PMXB and tested in the Agencourt CosMcPrep protocol modified to remove endotoxin (FIG. 1) using a 60 minute incubation with the cleared lysate before SPRI purification of plasmid DNA. Also included in the experiment were Magnesil silica beads and adsorbed PMXB/CM beads as controls.

Results

Figure 13:
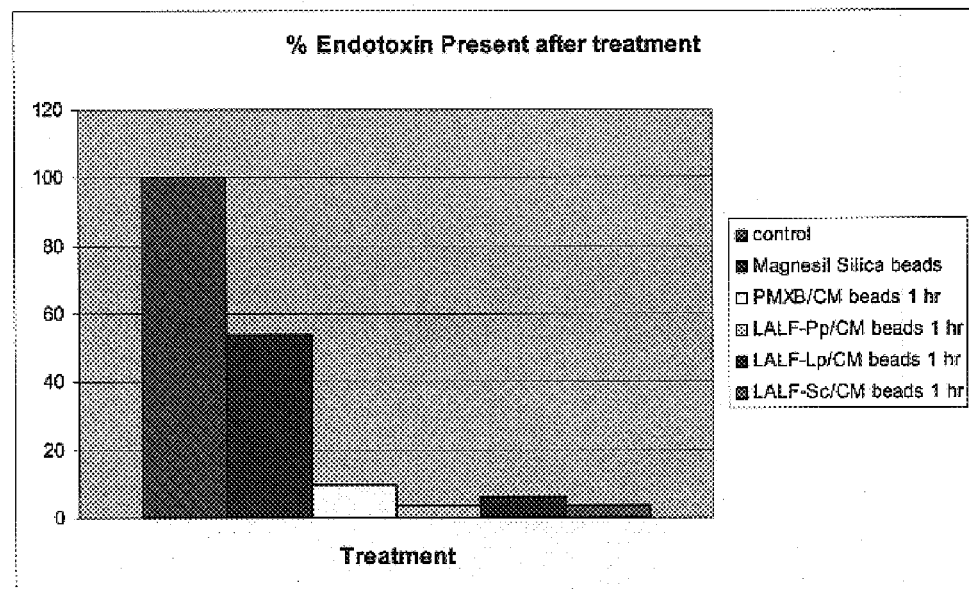
FIG. 13 is a bar graph showing endotoxin removal using LALF coupled CM beads.

The recombinant LALF's removed greater than 95% of the endotoxin from the plasmid DNA compared to untreated control, slightly better than the PMXB/CM beads in this experiment (FIG. 13). All three produced DNA containing less than 300 IU/mg plasmid DNA. FIG. 13 shows endotoxin removal using LALF coupled CM beads.

| Treatment | EU/mL | DNA mg/ml | EU/mg DNA | % EU of Control |
|---|---|---|---|---|
| Control | 2540.9 | 0.5 | 5286.1 | 100.0 |
| Magnesil silica beads | 1214.2 | 0.4 | 2844.3 | 53.8 |
| PMX-B/CM beads, 1 hr | 96.7 | 0.2 | 505.8 | 9.6 |
| LALF Pp/CM beads, 1 hr | 58.8 | 0.3 | 178.8 | 3.4 |
| LALF lP/CM beads, 1 hr | 65 | 0.3 | 257.9 | 4.9 |
| LALF Sc/CM beads, 1 hr | 50.0 | 0.3 | 183.4 | 3.5 |

EXAMPLE 8

Covalent Coupling of PMXB to CM Beads

To prevent PMXB contamination using our endotoxin removal scheme, PMXB is covalently coupled to CM beads.

Figure 14:
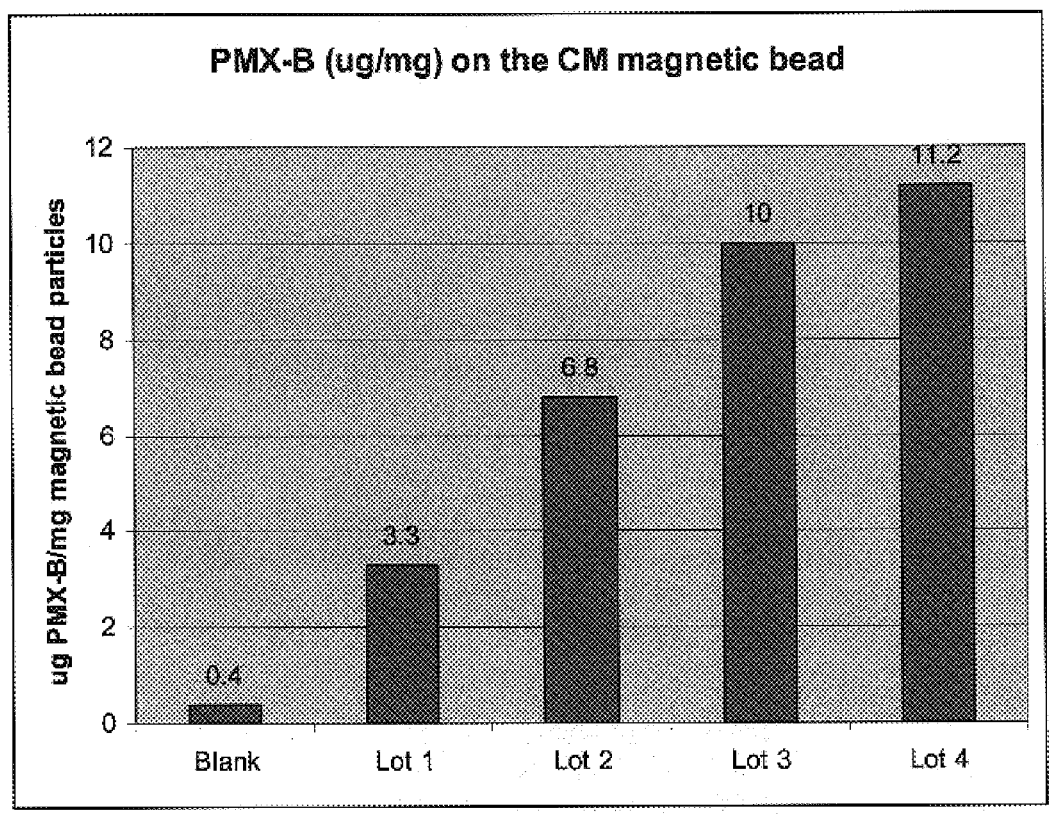
FIG. 14 is a bar graph showing preparation of PMX-B covalently coupled magnetic beads.
Figure 15:
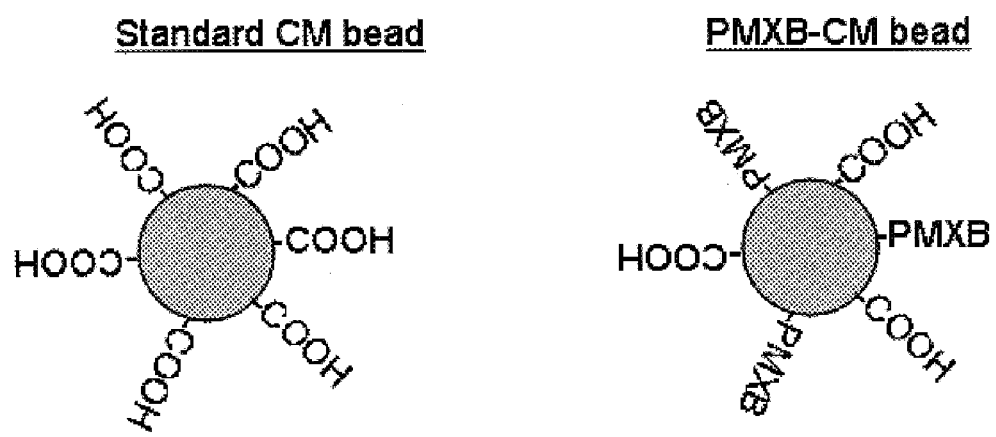
FIG. 15 is a schematic illustration of bi-functional PMXB-CM beads.

For direct coupling, carboxyl groups on the surface of the beads are first activated by carbodiimide 1-ethyl-3-(3-dimethylaminopropyl)-carbodiimide (EDAC) and then reacted with free amino groups on the protein. PMXB is titrated in the coupling reaction to optimize the amount of protein coupled to the surface. The amount of bound protein was determined by a copper reduction/bicinchoninic acid reaction (BCA). To distinguish between actual covalently attached protein and protein that is merely adsorbed to the surface, non-covalently associated protein is pre-eluted by treatment with a combination of base and detergent, a process which completely removes any adsorbed protein. The BCA protein assay is then used to measure the amount of protein remaining on the beads, and in solution. FIG. 14 shows the results of different coupling reaction using increasing amounts of PMX-B. FIG. 15 is a schematic illustration of the beads. FIG. 14 shows preparation of PMX-B covalently coupled magnetic beads. FIG. 15 is a schematic illustration of bi-functional PMXB-CM

EXAMPLE 9

Endotoxin Removal Using Bi-functional PMX-B/CM Beads

Figure 16:
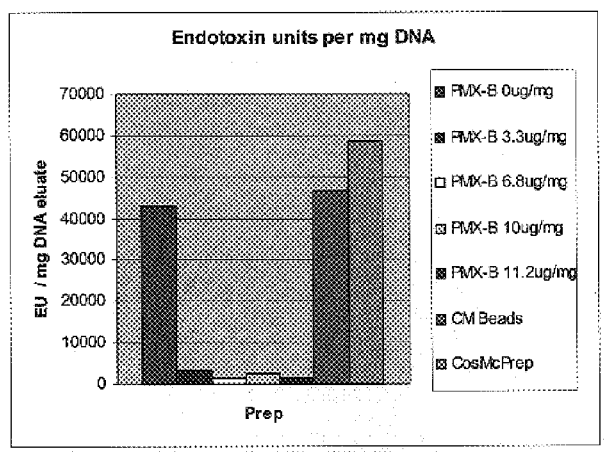
FIG. 16 is a bar graph showing removal of endotoxin from plasmid DNA with bifunctional PMXB-CM.

Bi-functional PMX-B beads from Example 8 were tested for the ability to remove endotoxin from plasmid preparations in conjunction with Agencourt's CosMcPrep DNA purification kit as illustrated in FIG. 10. Briefly, to each 240 uL of cleared lysate (FIG. 10, step 4), 100 uL PMXB-CM beads was added (containing differing amounts of PMXB). Following incubation and magnetic removal of the bi-functional beads, plasmid DNA in the supernatant was purified via SPRI (FIG. 10, steps 7-10). The amount of endotoxin in plasmid DNA preparations was determined by a photometric Limulus Amoebocyte Lysate (LAL) assay from BioWhittaker. The PMXB-CM beads remove over 97% of the associated endotoxin from the DNA preparation (FIG. 16). FIG. 16 shows removal of endotoxin from plasmid DNA with bifunctional PMXB-CM.

| | PMX-B 0 ug/mg | PMX-B 3.3 ug/mg | PMX-B 6.8 ug/mg | PMX-B 10 ug/mg | PMX-B 11.2 ug/mg | CM Beads | CosMcPrep |
|---|---|---|---|---|---|---|---|
| [DNA] in ng/ul + ug/ml | 386 | 405 | 344 | 338 | 406 | 626 | 536 |
| Total DNA in ug | 19.32 | 20.25 | 17.21 | 16.88 | 20.30 | 31.28 | 26.80 |
| EU LAL/ml eluate | 16580 | 1313 | 463 | 824 | 566 | 29092 | 31409 |
| EU LAL/ug DNA | 42.90 | 3.24 | 1.35 | 2.44 | 1.39 | 46.50 | 58.61 |
| EU LAL/mg DNA | 42903 | 3242 | 1346 | 2440 | 1395 | 46497 | 58608 |

EXAMPLE 10

Transfection of Endotoxin Free DNA Prepared with Bi-functional Beads

Figure 17A:
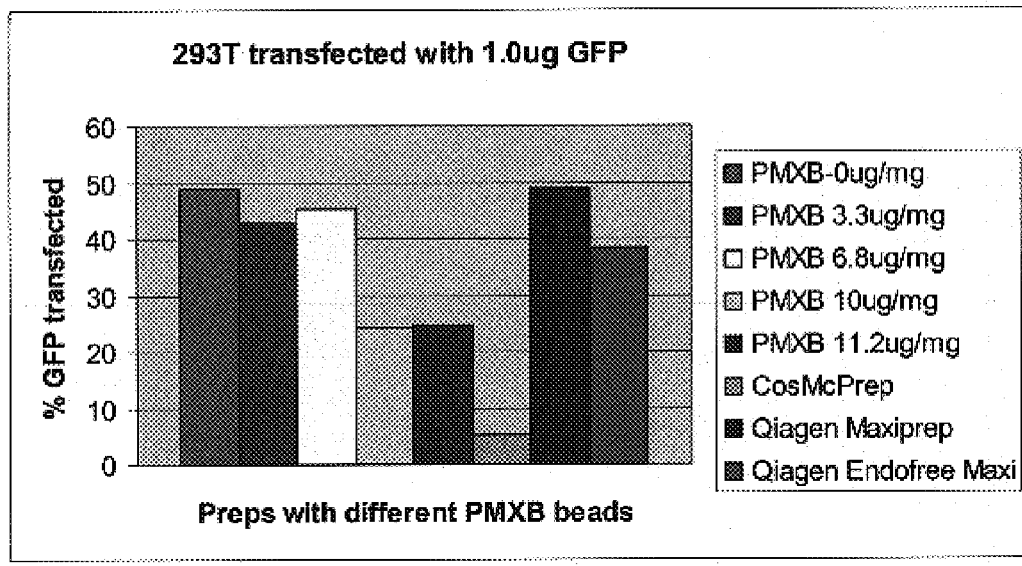
FIGS. 17A and 17B are bar graphs showing transfection of endotoxin free DNA prepared with bi-functional beads.
Figure 17B:
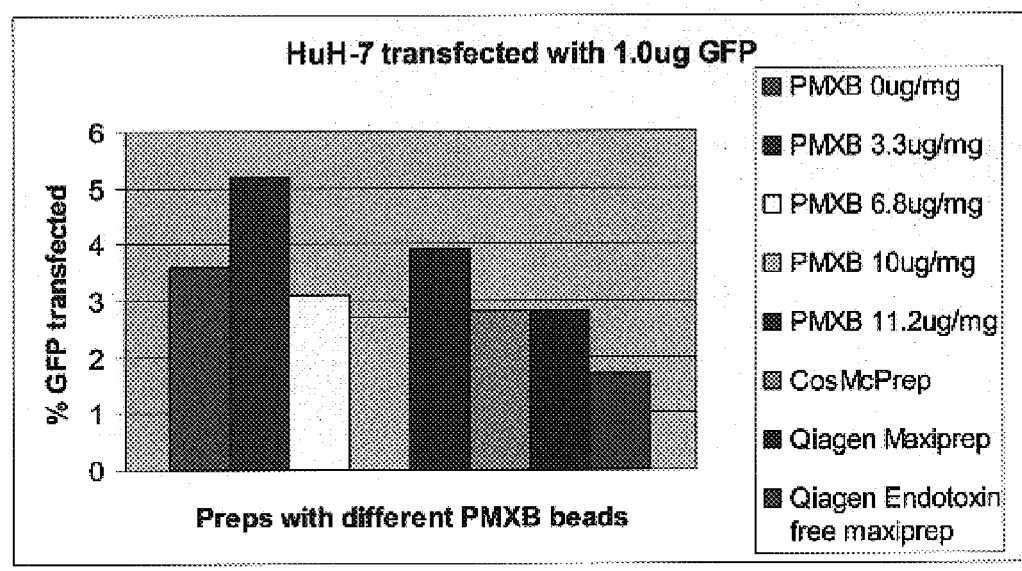

One microgram of pEGFP expression plasmid purified with PMX-B bifunctional beads were transfected into endotoxin insensitive 293T cells or endotoxin sensitive Huh-7 cells using Effectene reagent and Lipofectamine reagent respectively, according to the manufacturer's instructions. Forty-eight hours post transfection GFP fluorescence was measured with the Agilent Bioanalyzer 2100 cell chip. As expected, the relatively easily transfected 293 shows high expression among most of the preps (FIG. 17A). The difficult to transfect Huh-7 cells show lower expression (FIG. 17B). In both cases though, the PMXB-CM beads produce DNA that transfects as well as or better than Qiagen maxipreps or Qiagen Endofree maxipreps, which are considered Gold Standard in the industry.

Figure 18:
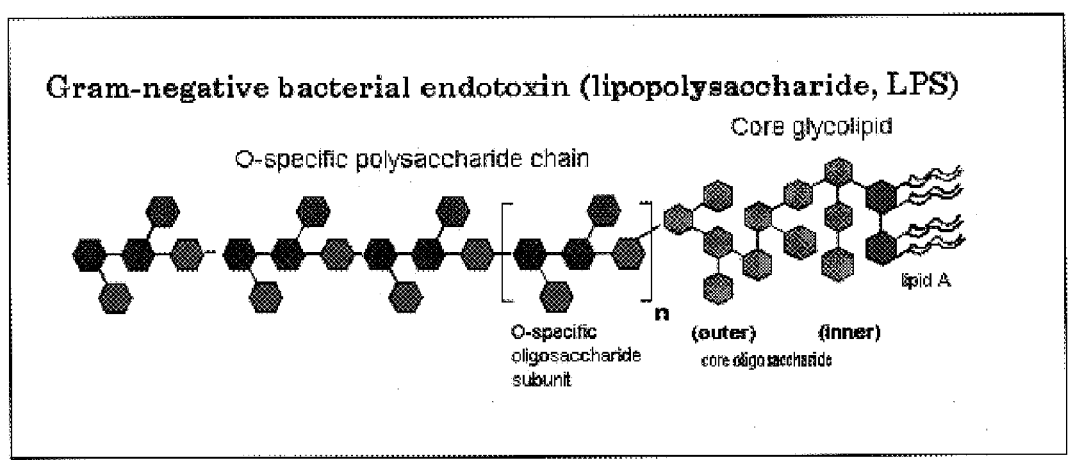
FIG. 18 shows the structure of lipopolysaccharide (LPS).
Figure 19:
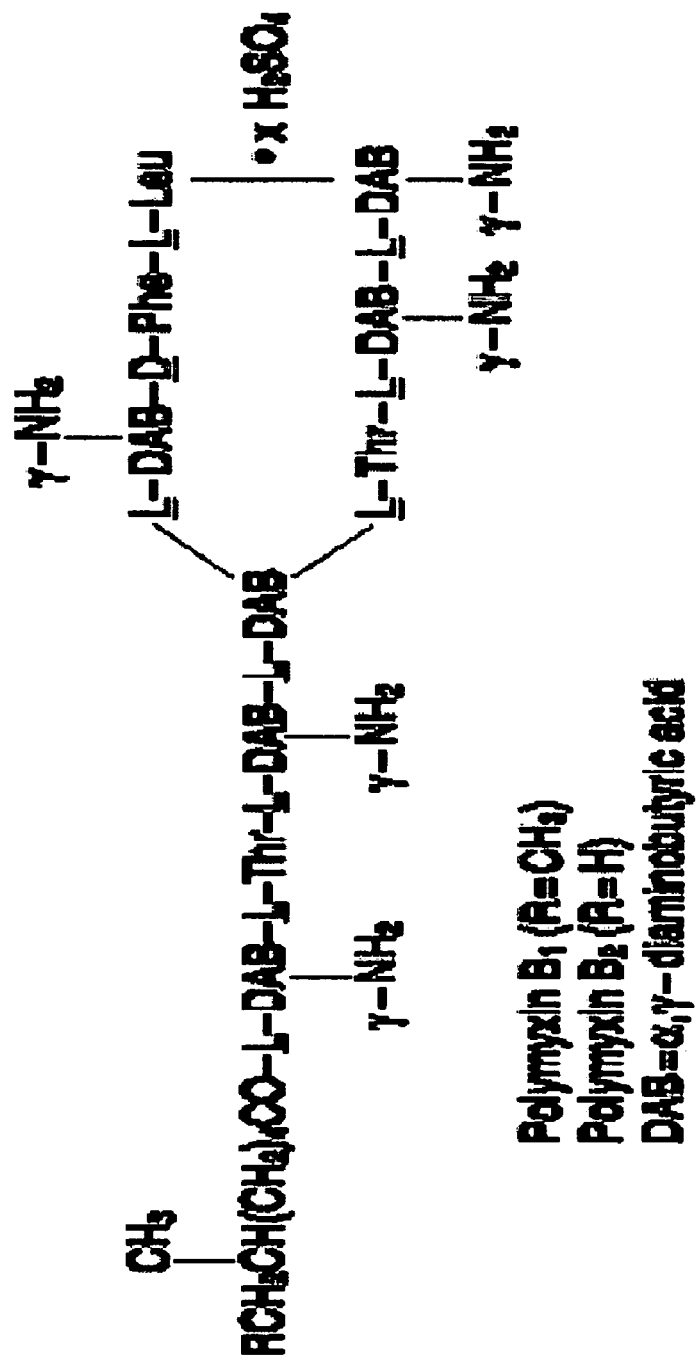
FIG. 19 shows that structure of polymyxin B (PMXB).

FIG. 18 shows the structure of lipopolysaccharide (LPS); FIG. 19 shows that structure of polymyxin B (PMXB).

EXAMPLE 11

Bi-functional Bead Application for Virus Purification

In another embodiment, the methods described herein can also be used to concentrate a virus from a solution and subsequently isolate viral nucleic acid. A polycationic polymer, such as the polymer polyethyleneimine (PEI) or poly-L-lysine (PLL), is covalently coupled to magnetic beads containing a carboxyl functional group. Carboxyl groups are first activated by carbodiimide 1-ethyl-3-(3-dimethylaminopropyl)-carbodiimide (EDAC) and then reacted with free amino groups on the polymer. This produces a bead with two functional groups, a polycation polymer for virus binding, and carboxyl groups for nucleic acid binding. The polymer modified bi-functional beads are added to a volume of virus containing serum or lysate and mixed well creating a first mixture in which viral particles in the serum are concentrated on the surface of the beads via interaction with the polymer. The beads are magnetically separated on a magnet and the serum supernatant is removed. To the beads are added a lysis buffer containing, for example, 20 mM Tris pH 7.0, 1% Triton-X-100, 2% SLS, 10 mM DTT, isopropanol and an RNase inhibitor. This results in a second mixture in which virus is lysed and viral nucleic acid becomes bound to the bead via interaction with the carboxyl groups. The beads are separated by a magnet, washed three times in a wash buffer and/or 70% ethanol. The beads are dried and the purified viral nucleic acid is eluted in a low ionic strength buffer.

EXAMPLE 12

PEI-Based Bead Virus Extraction

Procedure for Concentrating and Isolating Viral Nucleic Acid Using PEI-Carboxy Bi-Functional Beads.
1. Added 50 μl PEI carboxy beads (1% solid) to 1 ml plasma containing 50 to 10,000 HBV copies in an Eppendorf Tube. Mixed and incubated at room temperature for 10 minutes. The beads were captured by the magnet and the supernatant was discarded. The beads were resuspend beads in 200 μl water.
2. Added 400 μl Viral Lysis Solution (2 M GITC, 10 mM Tris pH 7.0, 1% NP-40, 10 mM DTT and 5 μg of poly A) to all samples. Mixed well.
3. Added 0.5 μg/μl of 20 mg/ml Proteinase K (17.9 mg protein/ml; 907 units/ml: Sigma P4850). Mixed and centrifuged briefly (~2 sec) to collect the contents at the bottom of the tube. Incubate at 55 C for 20 min. Kept on ice for 2 min.
4. Added 8 μl 30% final Isopropanol. Mixed the sample and incubated for 5 min. Centrifuged briefly (~2 sec) to collect tube contents.
5. Magnetically captured the beads, and discarded the supernatant.
6. Washed the beads twice with 400 μl Wash Buffer (14% PEG, 1M NaCl, 6M Urea).
7. Washed the beads three times with 400 μl 70% Ethanol and allowed the beads to dry at ambient temperature for 10 minutes.
8. Eluted the viral nucleic acid in 25 μl water. Magnetically captured the beads as in the previous steps and transferred the supernatant containing viral nucleic acid to a nuclease-free container.
9. The nucleic acid was amplified by nested PCR using gene specific primers.

Results

Figure 20:
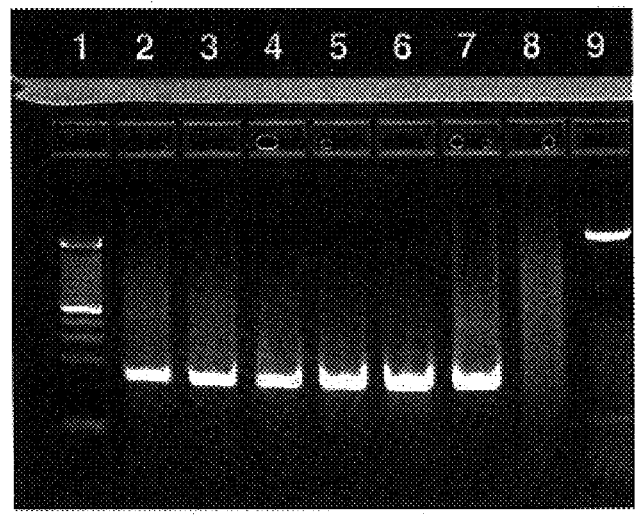
FIG. 20 is a gel showing isolation of virus using bifunctional solid phase carriers.

As shown in FIG. 20, the procedure was sensitive enough to detect down to 50 copies per ml of HBV.

EXAMPLE 13

Bi-functional Example of Globin Subtraction

Isolation of Total RNA from Human Whole Blood and Removal of Beta-Globin Specific Transcripts with Bi-Funtional Beads.

Figure 21:
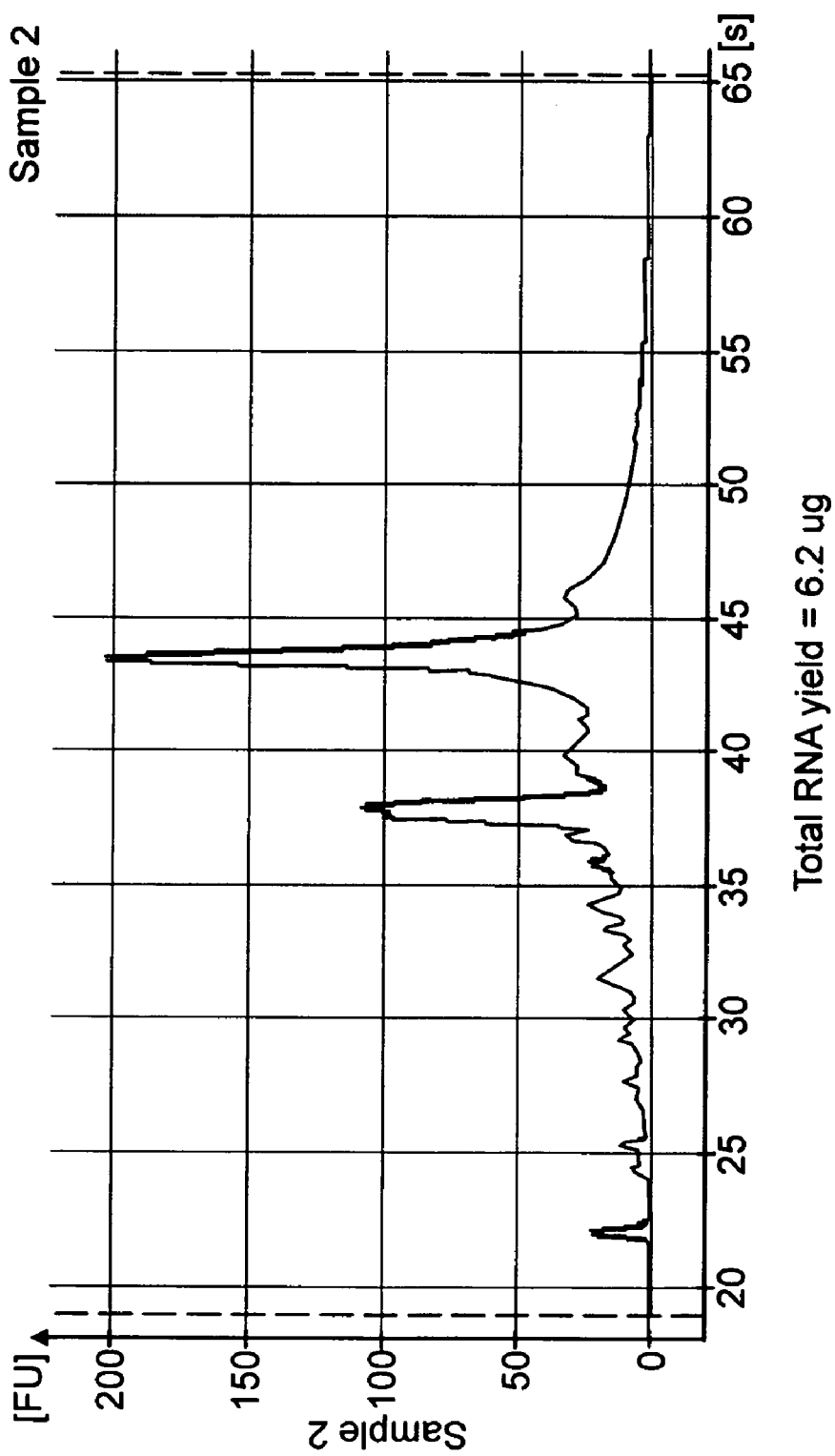
FIG. 21 shows an electropheregram of total RNA isolated from 0.3 mls human blood using this protocol.
Figure 22:
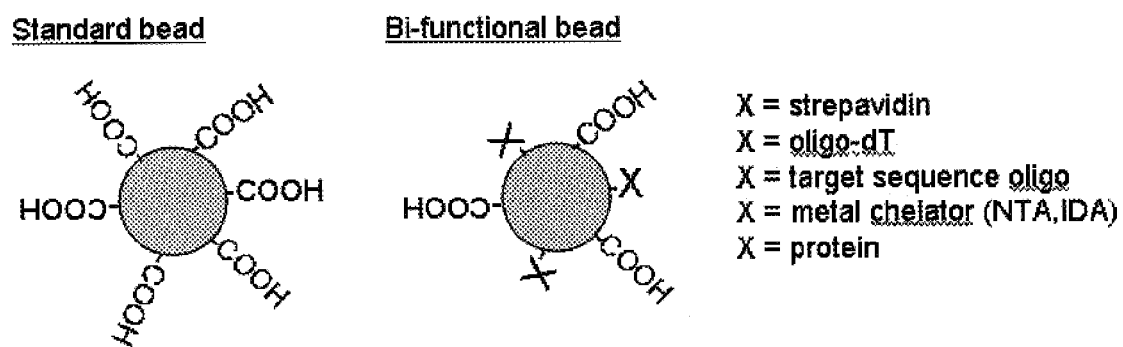
FIG. 22 is a schematic of a heteromultifunctional solid phase carrier.

One third volume of lysis buffer containing 4M GITC, 2 mM DTT, 2% Triton-X-100 and 0.4M sodium citrate is added to whole blood and mixed well. To the mixture is added an equal volume binding buffer comprising bi-functional magnetic beads and isopropanol. The bi-functional beads comprise strepavidin and carboxyl functional groups, to which a mixture of three biotinlylated oligos complementary in sequences to human beta globin mRNA transcript are attached via the biotin-strepavidin interaction. The beads are separated by a magnet and the supernatant is removed. The beads are washed with a first wash buffer comprising 2M GITC, 1 mM DTT, 1% Triton-X-100 and 0.2M sodium citrate and 30% isopropanol then three times by a second wash buffer comprising 70% ethanol. The beads are dried and then total RNA is eluted in a low ionic strength buffer. FIG. 21 shows an electropheregram of total RNA isolated from 0.3 mls human blood using this protocol. Total RNA was isolated with the method of the invention from 2.5 mls of human blood collected into PaxGene collection tubes.

To remove globin sequences, the elution buffer with the beads is adjusted to a final concentration of 0.5 M LiCl, 10 mM Tris, 1 mM EDTA, pH7.4, 0.1% LDS to promote binding of the oligonucleotide sequences to the complementary beta-globin RNA transcripts. The mixture is heated to 65 C for 5 minutes then cooled on ice. The hybridization occurs for 30 minutes at ambient temperature. The supernatant, which contains total blood RNA depleted of globin transcripts, is removed and saved. The extent of globin depletion was examined by performing quantitative RT-PCR on the supernatant from anti beta-globin beads and control bead hybridization that did not contain anti-globin oligos.

| Sample | Ct | % reduction |
|---|---|---|
| Negative Control Bead | 22.3 | 5.7 |
| anti-beta-globin bead | 23.4 | 62.6 |
| NTC | Undetermined | n/a |
| total RNA undiluted | 21.8825 | n/a |
| 1:1 dilution total RNA | 23.25393 | n/a |
| 1:5 dilution total RNA | 24.65676 | n/a |
| 1:10 dilution total RNA | 26.027063 | n/a |
| 1:20 dilution total RNA | 26.56443 | n/a |

In this experiment, it was possible to remove 62% of beta-globin sequence using an un-optimized mix of antisense beta-globin primers.

EXAMPLE 14

Globin Removal

Total RNA, 20 ug, in 0.5M LiCl, 10 mM Tris, 1 mM EDTA pH7.4, 0.1% LDS was combined with 10 pmol of biotin labeled oligonucleotides complementary to alpha and beta globin sequences in a final volume of 50 uL. The mixture was incubated for 30 minutes at 50 C. Bi-functional beads, 100 ug, containing carboxy and strepavidin groups were added to the mixture and incubated at room temperature for 30 minutes. Isopropanol was added to a final concentration of 30%. The beads washed three times with 70% ethanol, were placed on a magnet and the supernatant removed. RNA, minus globin sequences, was eluted with 20 mM LiCl. A globin specific quantitative RT-PCR assay was used to determine the amount of alpha and beta globin reduction compared to an internal beta-actin control RNA.

Results qRT-PCR results demonstrate that a majority of both the alpha globin and beta globin transcripts were removed using this protocol.

| Sample | Total (ug) | Concen (ng/ul) | β-actin Ct | β-globin Ct | % Reduction of β-globin | α-globin Ct | % Reduction of α-globin |
|---|---|---|---|---|---|---|---|
| Actin Control 1 | | | 27.1 | 15.5 | | 15.23 | |
| Sample 1 | 22 | 600 | 21.7 | 20.2 | 99.0% | 17.28 | 99.4% |
| Actin Control 2 | | | 26.8 | 15.4 | | 15.15 | |
| Sample 2 | 21 | 650 | 22.9 | 17.8 | 98.8% | 15.72 | 95.5% |

While this invention has been particularly shown and described with references to preferred embodiments thereof, it will be understood by those skilled in the art that various changes in form and details may be made therein without departing from the scope of the invention encompassed by the appended claims.

---

What is claimed is:

1. A method of selectively isolating a target species of nucleic acid molecule present in a mixture, comprising:
   a) combining the mixture with solid phase carriers having a surface comprising a first functional group which binds nucleic acids and a second functional group which selectively binds the target species of nucleic acid, thereby producing a first combination;
   b) maintaining the first combination under conditions appropriate for binding of the nucleic acids to the first functional group;
   c) separating the solid phase carriers from the first combination;
   d) combining the solid phase carriers with at least one agent that removes the nucleic acid from the first functional group of the solid phase carriers and binds the target species of nucleic acid to the second functional group of the solid phase carriers, thereby producing a second combination; and
   e) separating the solid phase carriers from the second combination, thereby isolating the target species of nucleic acid present in the mixture comprising nucleic acids.

2. The method of claim 1 wherein in step d) the solid phase carriers are combined with a first agent that removes the nucleic acid from the first functional group of the solid phase carriers, and a second agent that allows binding of the target species of nucleic acid to the second functional group of the solid phase carriers, thereby producing a second combination.

3. The method of claim 2 wherein the target species of nucleic acid is a nucleic acid species selected from the group consisting of: DNA, RNA and PNA.

4. The method of claim 2 wherein the first agent is a buffer comprising Tris, Tris and EDTA, formamide or a combination thereof.

5. The method of claim 4 wherein the buffer further comprises an enzyme selected from the group consisting of: DNase and Rnase.

6. The method of claim 2 wherein the solid phase carriers are magnetic microparticles.

7. The method of claim 2 wherein the first functional group is COOH and the second functional group is a nucleic acid sequence that is complementary to the target species of nucleic acid.

8. The method of claim 1 further comprising a step of lysing a cell, a host cell, an organism selected from the group consisting of a virus, a bacteria, a fungus, and a parasite, or a combination thereof, so as to release a target species of nucleic acid molecule.

9. A method of isolating mRNA present in a mixture comprising nucleic acids, comprising:
   a) combining the mixture with solid phase carriers having a surface comprising a first functional group which binds nucleic acids and a second functional group which selectively binds mRNA, thereby producing a first combination;
   b) maintaining the first combination under conditions appropriate for binding of the nucleic acids to the first functional group;
   c) separating the solid phase carriers from the first combination;
   d) combining the solid phase carriers with at least one agent that removes the nucleic acid from the first functional group of the solid phase carriers and binds the mRNA to the second functional group of the solid phase carriers, thereby producing a second combination; and
   e) separating the solid phase carriers from the second combination, thereby isolating mRNA present in a mixture comprising nucleic acids.

10. The method of claim 9 wherein in step d) the solid phase carriers are combined with a first agent that removes the nucleic acid from the first functional group of the solid phase carriers, and a second agent that allows binding of the mRNA to the second functional group of the solid phase carriers, thereby producing a second combination.

11. The method of claim 10 wherein the mixture is a biological sample.

12. The method of claim 11 wherein the biological sample is selected from the group consisting of: whole cells, tissue, a lysate and blood.

13. The method of claim 10 wherein the solid phase carriers are magnetic microparticles.

14. The method of claim 10 wherein the first functional group is COOH and the second functional group is selected from the group consisting of: oligo-dT, modified oligo-dT and a combination thereof.

15. The method of claim 10 wherein the buffer that elutes the nucleic acid from the first functional group of the solid phase carriers comprises water.

16. The method of claim 10 wherein the solid phase carriers are removed using a method selected from the group consisting of: applying a magnetic field, applying a vacuum and applying centrifugation.

17. The method of claim 10 which further comprises contacting the solid phase carriers with a wash buffer to remove contaminants prior to eluting the nucleic acid from the first functional group.

18. The method of claim 10 which further comprises contacting the solid phase carriers with an agent that digests DNA prior to eluting the nucleic acid from the first functional group of the solid phase carriers.

19. The method of claim 18 wherein the agent is DNase.

20. The method of claim 10 further comprising eluting the mRNA from the second functional group of the solid phase carriers.

21. The method of claim 20 wherein the mRNA is eluted in a buffer selected from the group consisting of: water, Tris, Tris and EDTA, and formamide.

22. A method of separating globin RNA from nucleic acid present in a mixture, comprising:
 a) combining the mixture with solid phase carriers having a surface comprising a first functional group which binds nucleic acids and a second functional group which selectively binds globin RNA, thereby producing a first combination;
 b) maintaining the first combination under conditions appropriate for binding of the nucleic acids to the first functional group;
 c) separating the solid phase carriers from the first combination;
 d) combining the solid phase carriers with at least one agent that removes the nucleic acid from the first functional group of the solid phase carriers and binds the globin RNA to the second functional group of the solid phase carriers, thereby producing a second combination; and
 e) separating the solid phase carriers from the second combination, thereby separating globin RNA present in a mixture comprising nucleic acids.

23. The method of claim 22 wherein in step d) the solid phase carriers are combined with a first agent that removes the nucleic acid from the first functional group of the solid phase carriers, and a second agent that allows binding of the globin RNA to the second functional group of the solid phase carriers, thereby producing a second combination.

24. The method of claim 22 wherein the solid phase carriers are magnetic microparticles.

25. The method of claim 22 wherein the first functional group is COOH and the second functional group is an oligonucleotide comprising a sequence that is complementary to a beta globin RNA sequence.

26. A method of separating globin RNA from nucleic acid present in a mixture, comprising:
 a) combining the mixture with biotin labeled oligonucleotides comprising sequences that are complementary to globin RNA sequences present in the mixture, thereby producing a first combination;
 b) maintaining the first combination under conditions in which hybridization occurs between the oligonucleotides and the globin RNA;
 c) combining the first combination with solid phase carriers having a first functional group that binds nucleic acid and a second functional group that selectively binds biotin, thereby producing a second combination;
 d) maintaining the second combination under conditions in which the nucleic acid binds to the first functional groups and the oligonucleotides which are hybridized to the globin RNA, bind to the second functional group of the solid phase carriers;
 e) separating the solid phase carriers from the second combination;
 f) combining the solid phase carriers with an agent that elutes the nucleic acid from the first functional group,
 thereby separating globin RNA from nucleic acid present in the mixture.

27. The method of claim 26 wherein the globin RNA is beta globin RNA.

28. A method of separating endotoxin from nucleic acid in a mixture, comprising:
 a) combining the mixture with solid phase carriers having a surface comprising a first functional group which binds nucleic acids and a second functional group which selectively binds endotoxin, thereby producing a first combination;
 b) maintaining the first combination under conditions appropriate for binding of the nucleic acids to the first functional group and endotoxin to the second functional group;
 c) separating the solid phase carriers from the first combination;
 d) combining the solid phase carriers with at least one agent that removes the nucleic acid from the first functional group of the solid phase carriers, thereby producing a second combination; and
 e) separating the solid phase carriers from the second combination,
 thereby separating endotoxin from nucleic acid present in the mixture.

29. The method of claim 28 wherein the solid phase carriers are magnetic microparticles.

30. The method of claim 29 wherein the first functional group is COOH and the second functional group is selected from the group consisting of: polymyxin B, native *Limulus* anti-LPS factor (LALF) and recombinant LALF.

31. A method of separating endotoxin from nucleic acid in a mixture comprising:
 a) combining the mixture with solid phase carriers having a surface comprising a first functional group which binds nucleic acids and a second functional group which selectively binds endotoxin, thereby producing a first combination;
 b) maintaining the first combination under conditions appropriate for binding of endotoxin to the second functional group;
 c) separating the solid phase carriers from the first combination;
 d) combining solid phase carriers having a surface comprising a functional group which binds nucleic acids with the first combination, thereby producing a second combination;
 e) maintaining the second combination under conditions appropriate for binding of nucleic acid to the functional group of the solid phase carriers of step d);
 f) separating the solid phase carriers from the second combination,
 thereby separating endotoxin from nucleic acid present in the mixture.

32. The method of claim 31 further comprising eluting the nucleic acid from the solid phase carriers of step f).

33. The method of claim 31 wherein the first functional group is COOH and the second functional group is selected from the group consisting of: polymyxin B, native *Limulus* anti-LPS factor (LALF) and recombinant LALF.

34. A method of isolating nucleic acid of an organism comprising:
 a) combining the organism with solid phase carriers having a surface comprising a first functional group which binds the organism and a second functional group that binds nucleic acid, thereby producing a first combination;
 b) maintaining the first combination under conditions in which the organism binds to the first functional group;
 c) separating the solid phase carriers from the first combination;
 d) combining the solid phase carriers with an agent that lyses the organism and binds the nucleic acid of the organism to the second functional group, thereby producing a second combination;
 e) maintaining the second combination under conditions in which the organism is lysed and the nucleic acid of the organism binds to the second functional group,
 thereby isolating the nucleic acid of the organism.

35. The method of claim 34 further comprising eluting the nucleic acid from the solid phase carriers of step e).

36. The method of claim 34 wherein the first functional group is COOH and the second functional group is polyethyleneimine.

37. A method of separating forward extension products and reverse extension products of a sequencing reaction comprising:
   a) combining a sequencing reaction mixture which comprises forward extension products and reverse extension products with solid phase carriers having a surface comprising a first functional group which selectively binds the forward extension products and a second functional group which binds nucleic acid, thereby producing a first combination;
   b) maintaining the first combination under conditions appropriate for binding of the forward extension products to the first functional group and binding of the reverse extension products to the second functional group;
   c) separating the solid phase carriers from the first combination;
   d) combining the solid phase carriers with a buffer that selectively elutes the reverse extension products from the second functional group of the solid phase carriers, thereby producing a second combination; and
   e) separating the solid phase carriers from the second combination,
   thereby separating forward extension products and reverse extension products of the sequencing reaction.

38. The method of claim 37 wherein the first functional group is streptavidin and the second functional group is COOH.

39. The method of claim 38 wherein the forward extension products are biotinylated.

40. The method of claim 37 wherein the solid phase carriers are magnetic microparticles.

41. The method of claim 37 wherein the solid phase carriers are removed using a method selected from the group consisting of: applying a magnetic field, applying a vacuum and applying centrifugation.

42. The method of claim 37 which further comprises contacting the solid phase carriers with a wash buffer to remove contaminants prior to eluting the reverse extension products from the second functional group.

43. The method of claim 37 wherein the buffer that selectively elutes the reverse extension products from the second functional group of the solid phase carriers is water.

44. The method of claim 37 further comprising eluting the forward extension products from the solid phase carriers of e).

45. The method of claim 44 further comprising sequencing the reverse extension products and the forward extension products.

46. A method of separating forward extension products and reverse extension products of a sequencing reaction comprising:
   a) combining a sequencing reaction mixture which comprises forward extension products and reverse extension products with solid phase carriers having a surface comprising a first functional group which selectively binds the forward extension products and a second functional group which binds nucleic acid, thereby producing a first combination;
   b) maintaining the first combination under conditions appropriate for binding of the forward extension products to the first functional group;
   c) separating the solid phase carriers from the first combination, thereby producing a second mixture comprising the reverse extension products;
   d) combining the solid phase carriers with a buffer that selectively elutes the forward extension products from the first functional group of the solid phase carriers, thereby producing a second combination;
   e) separating the solid phase carriers from the second combination;
   f) combining the solid phase carriers with the second mixture of c), thereby producing a third combination;
   g) maintaining the third combination under conditions appropriate for binding of the reverse extension products to the second functional group;
   h) separating the solid phase carriers from the third combination; and
   i) combining the solid phase carriers with a buffer that selectively elutes the reverse extension products from the second functional group of the solid phase carriers,
   thereby separating forward extension products and reverse extension products of the sequencing reaction.

* * * * *

SEQUENCE LISTING

```
<160> NUMBER OF SEQ ID NOS: 2

<210> SEQ ID NO 1
<211> LENGTH: 79
<212> TYPE: DNA
<213> ORGANISM: Unknown
<220> FEATURE:
<223> OTHER INFORMATION: sequencing results of a duplex sequencing
      reaction

<400> SEQUENCE: 1
ttctacgctc ggtacccggg gatcctctag agtcgacctg caggcatgca agcttgagta      60
ttctatagtg tcacctaaa                                                  79

<210> SEQ ID NO 2
<211> LENGTH: 74
<212> TYPE: DNA
<213> ORGANISM: Unknown
<220> FEATURE:
```

-continued

```
<223> OTHER INFORMATION: sequencing results of a duplex sequencing
      reaction

<400> SEQUENCE: 2
ttttacaacg tcgtgactgg gaaaaccctg gcgttaccca acttaatcgc cttgcagcac        60
atcccccttt cgcc                                                         74
```